(12) United States Patent
Hanessian et al.

(10) Patent No.: US 7,943,749 B2
(45) Date of Patent: May 17, 2011

(54) ANTIMICROBIAL 2-DEOXYSTREPTAMINE COMPOUNDS

(75) Inventors: Stephen Hanessian, Beaconsfield (CA); Janek Szychowski, Val Belair (CA); Susanta Sekhar Adhikari, Kankurgachi (IN); Kandasamy Pachamuthu, Montreal (CA); Michael T. Migawa, Carlsbad, CA (US); Richard H. Griffey, Vista, CA (US); Eric Swayze, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 748 days.

(21) Appl. No.: 11/740,998

(22) Filed: Apr. 27, 2007

(65) Prior Publication Data

US 2008/0045468 A1    Feb. 21, 2008

Related U.S. Application Data

(63) Continuation of application No. PCT/US2005/040364, filed on Nov. 7, 2005.

(60) Provisional application No. 60/625,440, filed on Nov. 5, 2004.

(51) Int. Cl.
*C07H 15/20* (2006.01)
*C07H 15/22* (2006.01)
*A01N 43/04* (2006.01)
*A61K 31/70* (2006.01)

(52) U.S. Cl. .......................................... 536/13.2; 514/39

(58) Field of Classification Search ........................ None
See application file for complete search history.

(56) References Cited

U.S. PATENT DOCUMENTS

| | | | | |
|---|---|---|---|---|
| 3,808,198 | A | 4/1974 | Naito et al. | 260/210 AB |
| 3,860,574 | A | 1/1975 | Naito et al. | 260/210 NE |
| 3,896,106 | A | 7/1975 | Naito et al. | 260/210 AB |
| 3,897,412 | A | 7/1975 | Naito et al. | 260/210 AB |
| 3,956,274 | A | 5/1976 | Umezawa et al. | |
| 4,066,753 | A * | 1/1978 | Hanessian | 514/39 |
| 4,347,354 | A | 8/1982 | Cron et al. | 536/10 |
| 4,424,343 | A | 1/1984 | Cron et al. | 536/13.8 |
| 5,534,408 | A | 7/1996 | Green et al. | 435/5 |
| 5,935,776 | A | 8/1999 | Green et al. | 435/5 |
| 2004/0229265 | A1 | 11/2004 | Lapidot et al. | 435/6 |
| 2005/0148522 | A1 | 7/2005 | Baasov et al. | 514/36 |
| 2008/0214845 | A1 | 9/2008 | Migawa et al. | 549/415 |
| 2008/0293649 | A1 | 11/2008 | Swayze et al. | 514/39 |
| 2008/0300199 | A1 | 12/2008 | Linsell et al. | 514/38 |

FOREIGN PATENT DOCUMENTS

| | | |
|---|---|---|
| FR | 1.361.393 | 4/1964 |
| FR | 2.183.236 | 12/1973 |
| GB | 1 400 676 | 7/1975 |
| GB | 1 456 674 | 11/1976 |
| GB | 1488420 | 10/1977 |
| GB | 2068366 A | 8/1981 |
| JP | 49-101355 | 9/1974 |
| JP | 52-100464 | 8/1977 |
| WO | WO 92/02530 A1 | 2/1992 |
| WO | WO 03/059246 A2 | 7/2003 |
| WO | WO 2005/041984 A1 | 5/2005 |
| WO | WO 2006/052930 A1 | 5/2006 |
| WO | WO 2007/028012 A2 | 3/2007 |
| WO | WO 2007/064954 A2 | 6/2007 |

OTHER PUBLICATIONS

Battistini et al., "Semisynthetic Aminoglycoside Antibiotics. IV 3',4'-Dideoxyparomomycin and Analogues," *J. of Antibiotics* 35(1): 98-101, Jan. 1982.

Greenberg et al., "Design and Synthesis of New Aminoglycoside Antibiotics Containing Neamine as an Optimal Core Structure: Correlation of Antibiotic Activity with in Vitro Inhibition of Translation," *J. Am. Chem. Soc.* 121(28): 6527-6541, 1999.

Hanessian and Vatele, "Aminoglycoside Antibiotics 4'-Deoxyneomycin and 4'-Deoxyparomamine," *Journal of Antibiotics* 33(6): 675-678, Jun. 1980.

Hermansky, "Neomycin N-methanesulfonate," Database CAPLUS on STN, Accession No. 60:11121, 1962, 2 pages.

Kondo et al., "Crystal Structure of the Bacterial Ribosomal Decoding Site Complexed with a Synthetic Doubly Functionalized Paromomycin Derivative: a New Specific Binding Mode to an A-minor Motif Enhances in vitro Antibacterial Activity," *ChemMedChem* 2: 1631-1638, 2007.

Li et al., "Investigation of the Regioselectivity for the Staudinger Reaction and Its Application for the Synthesis of Aminoglycosides with N-1 Modification," *J. Org. Chem.* 72(11): 4055-4066, 2007.

Marrero-Ponce et al., "Non-stochastic and stochastic linear indices of the molecular pseudograph's atom-adjacency matrix: a novel approach for computational in silico screening and 'rational' selection of new lead antibacterial agents," *J. Mol. Model.* 12: 255-271, 2006.

Marrero-Ponce et al., "Atom, atom-type, and total nonstochastic and stochastic quadratic fingerprints: a promising approach for modeling of antibacterial activity," *Biooorganic & Medicinal Chemistry* 13: 2881-2899, 2005.

Narita et al., "Synthesis and Activity of Butirosin Derivatives with 5"-Amidino and 5"-Guanidino Substituents," *Journal of Antibiotics* 44(1): 86-92, Jan. 1991.

Shier and Rinehart, Jr., "Chemistry and Biochemistry of the Neomycins. XVI Synthesis and Bioactivity of Hexa-N-Benzylneomycins," *Journal of Antibiotics* 26(10): 547-550, Oct. 1973.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Org. Lett.* 1(6): 953-956, 1999.

Takamoto and Hanessian, "Aminoglycoside Antibiotics: Chemical Transformation of Paromomycin Into a Bioactive Pseudotrisaccharide," *Tetrahedron Letters* 46: 4009-4012, 1974.

Takeda et al., "Mutational Biosynthesis of Butirosin Analogs II. 3',4'-Dideoxy-6'-N-Methylbutirosins, New Semisynthetic Aminoglycosides," *Journal of Antibiotics* 31(10): 1031-1038, Oct. 1978.

Takeda et al., "Mutational Biosynthesis of Butirosin Analogs III. 6'-N-Methylbutirosins and 3',4'-Dideoxy-6'-C-Methylbutirosins, New Semisynthetic Aminoglycosides," *Journal of Antibiotics* 31(10): 1039-1045, Oct. 1978.

(Continued)

*Primary Examiner* — Layla Bland

(57) ABSTRACT

The present invention is directed to analogs of paromomycin having a variety of chemical functional groups attached at the 2"-O-position as well as their preparation and use as prophylactic or therapeutics against microbial infection.

23 Claims, No Drawings

OTHER PUBLICATIONS

Watanabe et al., "Synthesis of 6'-Amino-1-*N*-[(*S*)-4-Amino-2-Hydroxybutyryl]-6'-Deoxylividomycin A," *Bulletin of the Chemical Society of Japan* 48(8): 2303-2305, 1975.

Watanabe et al., "Synthesis of 1-*N*-[(*S*)-4-Amino-2-hydroxybutyryl-]lividomycin A," *Bulletin of the Chemical Society of Japan* 48(7): 2124-2126, 1975.

Watanabe et al., "Synthesis of 1-N-((*s*)-4-Amino-2-Hydroxybutyryl) Lividomycin A," *Journal of Antibiotics* 26(5): 310-312, May 1973.

The Merck Index, twelfth edition. Budavari (ed.), Whitehouse Station: Merck & Co., Inc., Compound 1559, 1996.

Alper et al., "Probing the Specificity of Aminoglycoside—Ribosomal RNA Interactions with Designed Synthetic Analogs", Journal of American Chemical Society 120(9): 1965-1978, 1998.

Chow and Bogdan, "A Structural Basis for RNA-Ligand Interactions", Chemical Reviews 97(5): 1489-1513, 1997.

Francois et al., "Antibacterial Aminoglycosides with a Modified Mode of Binding to the Ribosomal-RNA Decoding Site", Angewandte Chemie Int. Ed. 43: 6735-6738, 2004.

Hanessian et al., "Aminoglycoside antibiotics: Chemical conversion of neomycin B, paromomycin, and lividomycin B into bioactive pseudosaccharides", Canadian Journal of Chemistry 56(11): 1482-1491, Jun. 1, 1978.

Moazed and Noller, "Interaction of antibiotics with functional sites in 16S ribosomal RNA", Nature 327: 389-394, Jun. 4, 1987.

Pénasse et al., "Sur quelques dérivés mono N-alcoylés de la néomycine et de la paromomycine", Bulletin de la Societe chimique de France 7(415): 2391-2394, Jul. 1969.

Sunada et al., "Enzymatic 1-N-Acetylation of Paromomycin by an Actinomycete Strain #8 with Multiple Aminoglycoside Resistance and Paromomycin Sensitivity", The Journal of Antibiotics 52(9): 809-814, Sep. 1999.

Taniyama et al., "Antibiotics Aminosidin. II. Some Amino Derivatives of Aminosidin and Their Biological Activity", Chemical & Pharmaceutical Bulletin 21(3): 609-615, Mar. 1973.

Tok et al., "Binding of Aminoglycoside Antibiotics with Modified A-site 16S rRNA Construct Containing Non-Nucleotide Linkers", Bioorganic & Medicinal Chemistry Letters 12: 365-370, 2002.

Wallis and Schroeder, "The Binding of Antibiotics to RNA", Progress in Biophysics and Molecular Biology, 67 (2/3): 141-154, 1997.

Watanabe et al., "Synthesis of 6'-amino-6'-deoxylvidomycin B and 6'-deoxy-6'-methylamino- and 6'-deoxy-6'-(2-hydroxyethylamino)-lividomycin B", The Journal of Antibiotics 26(12): 802-804, Dec. 1973.

* cited by examiner

ANTIMICROBIAL 2-DEOXYSTREPTAMINE COMPOUNDS

CROSS-REFERENCE TO RELATED APPLICATIONS

This application is a continuation of PCT International Patent Application No. PCT/US2005/040364, which was filed in the U.S. Receiving Office of the PCT on Jul. 11, 2005, now pending, which claims the benefit under 35 U.S.C. §119 (e) of U.S. Provisional Patent Application No. 60/625,440 filed May 11, 2004. These applications are incorporated herein by reference in their entireties.

FIELD OF THE INVENTION

A particular interest in modern drug discovery is the development of novel low molecular weight drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, their production can be inhibited by interfering with the translation of their mRNAs. Since both the proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of biologically active proteins for screening is a major limitation in classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (Chow, C. S.; Bogdan, F. M., Chem. Rev., 1997, 97, 1489, Wallis, M. G.; Schroeder, R., Prog. Biophys. Molec. Biol. 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (Alper, P. B.; Hendrix, M.; Sears, P.; Wong, C., J. Am. Chem. Soc., 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers) that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity these ancient processes fundamental to all bacterial life represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested a pattern of sensitivity and resistance is usually defined. Unfortunately, this spectrum of activity can subsequently change to a remarkable degree, because microorganisms have evolved an array of ingenious alterations discussed above that allow them to survive in the presence of antibiotics. The mechanism of drug resistance varies from microorganism to microorganism and from drug to drug.

The development of resistance to antibiotics usually involves a stable genetic change, heritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, there is a need for new chemical entities that possess antimicrobial activity. Further, in order to accelerate the drug discovery process, new methods for synthesizing aminoglycoside antibiotics are needed to provide an array of compounds that are potentially new drugs for the treatment microbial infections.

BRIEF SUMMARY OF THE INVENTION

In one aspect of the present invention aminoglycoside compounds having formula I are provided:

wherein:
each $R_1$ is, independently, H or a hydroxyl protecting group;
each $R_2$ and $R_3$ is, independently, H, an amino protecting group or together $R_2$ and $R_3$ that are connected to the same nitrogen atom form a cyclic protecting group that can include additional heteroatoms selected from N, O and S;
Z is an optionally linked chemical functional group; and
wherein said optionally linked chemical functional group is other than benzyl, benzoyl, acetyl or other hydroxyl protecting group.

In one embodiment the optionally linked chemical functional group has the formula:

$$-[C(G_1)(G_2)_{r1}]_m-(L_1)_n-[C(G_1)(G_2)_{r2}]_{mm}-Q_1$$

wherein:
$L_1$ is S, O, C(H)J_3 or NJ_1;
each $G_1$ and $G_2$ is, independently, H, halogen, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl or substituted $C_2$-$C_{20}$ alkynyl;
m is from 1 to about 8;
mm is 0 or from 1 to about 8;
n is 0 or from 1 to about 8;
each r1 and r2 is, independently, 0 or 1;
$Q_1$ is H, halogen, $OJ_1$, $NJ_1J_2$, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, heteroaryl, substituted heteroaryl, a heterocycle radical, a substituted heterocycle radical, a conjugate group, a reporter group, or a substituted or unsubstituted mono or poly cyclic structure that can be unsaturated, partially saturated or fully saturated and can include one or more heteroatoms selected from O, N and S and wherein said mono or poly cyclic structure is bonded directly or through said substituent group;

each of said substituted groups, is, independently, mono or poly substituted with optionally protected substituent groups independently selected from halogen, mono, di or trihaloalkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, heteroaryl, substituted heteroaryl, a heterocycle radical, a substituted heterocycle radical, $OJ_1$, $NJ_1J_2$, $N_3$, COOH, $C(O)J_3$, =O, CN, $NO_2$, $SJ_1$, $S(O)J_1$, $S(O)_2J_1$, $C(O)NJ_1J_2$, N(H)C(O)$J_1$, $N(J_1)(CH_2)_{mn}OJ_1$ and $N(J_1)(CH_2)_{mn}NJ_1J_2$, a conjugate group or a substituted or unsubstituted mono or poly cyclic structure that can be unsaturated, partially saturated or fully saturated and can include one or more heteroatoms selected from O, N and S;

each $J_1$ and $J_2$ is, independently, H, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, $C(O)J_3$, a protecting group or an optionally linked conjugate group;

each $J_3$ is, independently, H, hydroxyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, a protecting group or an optionally linked conjugate group; and mn is from 1 to about 8.

In one embodiment each $R_1$ is a hydroxyl protecting group. In another embodiment each $R_1$ is H. In a further embodiment each $R_2$ is an amino protecting group and each $R_3$ is H, or optionally $R_2$ and $R_3$ that are connected to the same nitrogen atom form a cyclic protecting group that may include additional heteroatoms selected from N, O and S.

In one embodiment each $R_1$, $R_2$ and $R_3$ is H. In another embodiment m is from 2 to 8. In a further embodiment n is 1.

In one embodiment the sum of m and mm is from 3 to 8. In another embodiment the sum of m and mm is from 3 to 8 and n is 1. In a further embodiment the sum of m and mm is from 3 to 8, n is 1 mm is from 1 to 8.

In one embodiment m is 2, n is 1, and $L_1$ is $NJ_3$. In another embodiment m is 2, n is 1, $L_1$ is $NJ_3$ and mm is from 1 to 4. In another embodiment m is 2, n is 1, $L_1$ is $NJ_3$, mm is from 1 to 4 and $Q_1$ is H, amino, substituted amino, alkylamino, substituted alkylamino, a conjugate group, a reporter group, or a substituted or unsubstituted mono or poly cyclic structure that can be unsaturated, partially saturated or fully saturated and can include one or more heteroatoms selected from O, N and S with a preferred substituted or unsubstituted mono or poly cyclic structure comprising one or more fused or linked rings wherein each ring is, independently, alicyclic, heterocyclic, aryl or heteroaryl.

In one embodiment $Q_2$ is phenyl, biphenyl, benzoyl, adamanthanyl, a steroidyl group, 1,8-naphthalenedicarboximide, pyridinyl, piperidinyl, piperazinyl, benzimidazolyl, imidazolyl, pyrrolidinyl, pyrazolyl, indolyl, 1H-indazolyl, α-carbolinyl, carbazolyl, phenothiazinyl, phenoxazinyl, quinolinyl, tetrazolyl, triazolyl, and morpholinyl.

In one embodiment m is from 1 to 5. In another embodiment m is from 1 to 5 and n is 0. In a further embodiment m is from 1 to 5, n is 0 and mm is 0. In yet a further embodiment m is from 1 to 5, n is 0, mm is 0 and $Q_1$ is H, amino, substituted amino, alkylamino, substituted alkylamino, a conjugate group, a reporter group, or a substituted or unsubstituted mono or poly cyclic structure that can be unsaturated, partially saturated or fully saturated and can include one or more heteroatoms selected from O, N and S with a preferred list of substituted or unsubstituted mono or poly cyclic structure comprising one or more fused or linked rings wherein each ring is, independently, alicyclic, heterocyclic, aryl or heteroaryl with a more preferred list including a heterocycle radical, aryl or a heteroaryl group.

In one embodiment m is 2. In another embodiment m is 2, n is 1 and $L_1$ is $NJ_1$. In another embodiment m is 2, n is 1, $L_1$ is $NJ_1$ and mm is from 1 to 4.

In one embodiment each $G_1$ and $G_2$ is H.

In one embodiment the optionally linked chemical functional group has the formula:

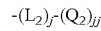

wherein:

$L_2$ is a linking group or a substituted linking group;

each $Q_2$ is, independently, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $OJ_1$, $NJ_1J_2$, $N_3$, $C(=O)OJ_3$, $C(=O)J_3$, =O, CN, $NO_2$, $SJ_1$, =$NJ_1$, $C(=O)NJ_1J_2$, —$N(J_1)C(=O)J_3$), $OC(=O)NJ_1J_2$, $N(J_1)C(=O)OJ_1$, $N(J_1)C(=O)NJ_1J_2$, $N(J_1)C(S)NJ_1J_1$, $N(J_1)C(=NJ_1)NJ_1J_2$, $C(=NJ_1)NJ_1J_2$, $C(=NJ_1)J_1$, $S(O)J_1$, $S(O)_2J_1$, $S(O)_2NJ_1J_2$, $N(J_1)S(O)_2J_1$, $N(J_1)(CH_2)_{nm}$—$OJ_1$, $N(J_1)(CH_2)_{nm}NJ_1J_2$, a conjugate group, a reporter group, $C_5$-$C_{20}$ aryl, substituted $C_5$-$C_{20}$ aryl, alicyclyl, substituted alicyclyl, heteroaryl, substituted heteroaryl, a heterocycle radical, a substituted heterocycle radical or a substituted or unsubstituted mono or poly cyclic structure that can be unsaturated, partially saturated or fully saturated and can include one or more heteroatoms selected from O, N and S, wherein said mono or poly cyclic structure is bonded directly or through said substituent group; and wherein each of said $Q_2$ can be further mono or poly substituted with one or more substituent groups.

j is 0 or 1;

jj is from 1 to about 4;

wherein each of said substituted groups are mono or poly substituted with substituent groups independently selected from halogen, trifluoromethyl, trifluoroalkoxy, $NHNH_2$, $ONH_2$, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $OJ_1$, $NJ_1J_2$, $N_3$, =$NJ_1$, $C(=O)OJ_3$, $C(=O)J_3$, =O, CN, $NO_2$, $SJ_1$, $C(=O)NJ_1J_2$, $N(J_1)C(=O)J_3$, $OC(=O)NJ_1J_2$, $N(J_1)C(=O)OJ_1$, $N(J_1)C(=O)NJ_1J_2$, $N(J_1)C(S)NJ_1J_1$, $N(J_1)C(=NJ_1)NJ_1J_2$, $C(=NJ_1)NJ_1J_2$, $J_1C(=NJ_1)J_1$, $S(O)J_1$, $S(O)_2J_1$, $S(O)_2NJ_1J_2$, $N(J_1)S(O)_2J_1$, $N(J_1)$-$(CH_2)_{nm}$—$OJ_1$, $N(J_1)$-$(CH_2)_{nm}$—$NJ_1J_2$, a conjugate group, a reporter group, a metal coordination group, an amino acid side chain, a carbohydrate, a drug, or a group capable of hydrogen bonding, $C_5$-$C_{20}$ aryl, substituted $C_5$-$C_{20}$ aryl, $C_5$-$C_{20}$ alicyclic, substituted $C_5$-$C_{20}$ alicyclic, heteroaryl, substituted heteroaryl, a heterocycle radical, a substituted heterocycle radical or a substituted or unsubstituted, linked, fused or mixed, mono or poly cyclic structure that can be unsaturated, partially saturated or fully saturated and can include one or more heteroatoms selected from O, N and S, wherein said mono or poly cyclic structure is bonded directly or through said substituent group;

each $J_1$ and $J_2$ is, independently, H, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, C(=O)$J_3$, a protecting group, an optionally linked conjugate group or a substituent group;

each $J_3$ is, independently, H, hydroxyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, a protecting group, an optionally linked conjugate group or a substituent group; and mn is from 1 to about 8.

In one embodiment j and jj are each 1. In another embodiment j is 1 and $L_2$ is $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl or substituted $C_2$-$C_{20}$ alkynyl, wherein each of said alkyl, alkenyl and alkynyl groups can include one or more heteroatoms selected from —O—, O=, S or N($J_1$).

The present invention also provides for compounds having the stereochemistry as defined below:

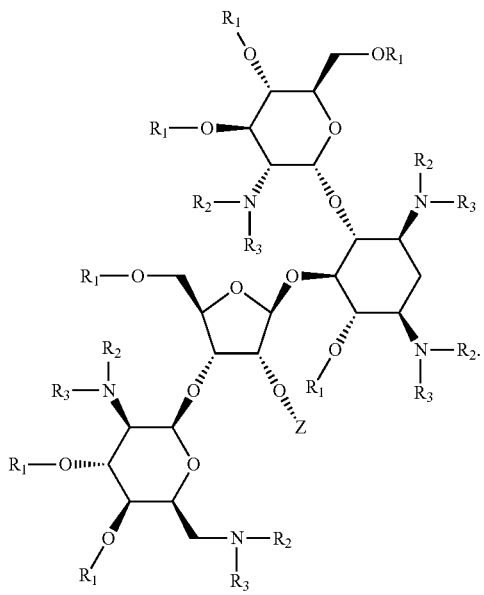

The present invention also provides methods of using the described compounds in therapy.

DETAILED DESCRIPTION OF THE INVENTION

The present invention provides aminoglycoside compounds having formula I:

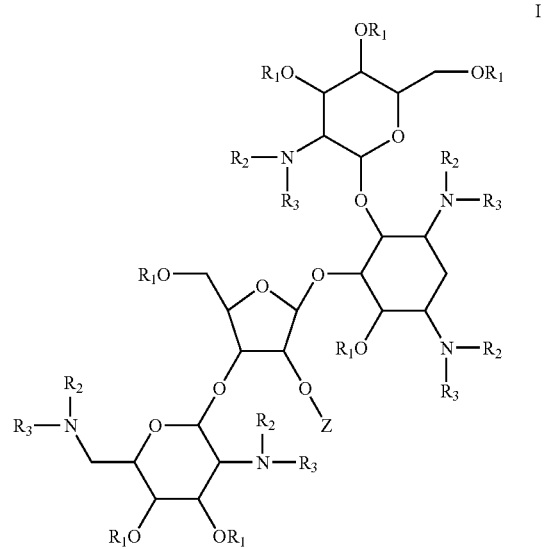

wherein:
each $R_1$ is, independently, H or a hydroxyl protecting group;
each $R_2$ and $R_3$ is, independently, H, an amino protecting group or together $R_2$ and $R_3$ that are connected to the same nitrogen atom form a cyclic protecting group that can include additional heteroatoms selected from N, O and S;
Z is an optionally linked chemical functional group; and
wherein said optionally linked chemical functional group is other than benzyl, benzoyl, acetyl or other hydroxyl protecting group.

The optionally linked chemical functional group can have one of formulas:

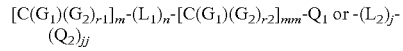

wherein:
$L_1$ is S, O, C(H)$J_3$ or N$J_1$;
each $G_1$ and $G_2$ is, independently, H, halogen, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl or substituted $C_2$-$C_{20}$ alkynyl;
m is from 1 to about 8;
mm is 0 or from 1 to about 8;
n is 0 or from 1 to about 8;
each r1 and r2 is, independently, 0 or 1;
$Q_1$ is H, halogen, $OJ_1$, $NJ_1J_2$, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, heteroaryl, substituted heteroaryl, a heterocycle radical, a substituted heterocycle radical, a conjugate group, a reporter group, or a substituted or unsubstituted mono or poly cyclic structure that can be unsaturated, partially saturated or fully saturated and can include one or more heteroatoms selected from O, N and S and wherein said mono or poly cyclic structure is bonded directly or through said substituent group;
each of said substituted groups, is, independently, mono or poly substituted with optionally protected substituent groups independently selected from halogen, mono, di or trihaloalkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, heteroaryl, substituted heteroaryl, a heterocycle radical, a substituted heterocycle radical, $OJ_1$, $NJ_1J_2$, $N_3$, COOH, C(O)$J_3$, =O, CN, $NO_2$, $SJ_1$, S(O)$J_1$, S(O)$_2J_1$, C(O)N$J_1J_2$, N(H)C(O)

$J_1$, $N(J_1)(CH_2)_{mn}OJ_1$ and $N(J_1)(CH_2)_{mn}NJ_1J_2$, a conjugate group or a substituted or unsubstituted mono or poly cyclic structure that can be unsaturated, partially saturated or fully saturated and can include one or more heteroatoms selected from O, N and S;

each $J_1$ and $J_2$ is, independently, H, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, $C(O)J_3$, a protecting group or an optionally linked conjugate group;

each $J_3$ is, independently, H, hydroxyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, a protecting group or an optionally linked conjugate group; and mn is from 1 to about 8.

$L_2$ is a linking group or a substituted linking group;

each $Q_2$ is, independently, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $OJ_1$, $NJ_1J_2$, $N_3$, $C(=O)OJ_3$, $C(=O)J_3$, $=O$, CN, $NO_2$, $SJ_1$, $=NJ_1$, $C(=O)NJ_1J_2$, $-N(J_1)C(=O)J_3$, $OC(=O)NJ_1J_2$, $N(J_1)C(=O)OJ_1$, $N(J_1)C(=O)NJ_1J_2$, $N(J_1)C(S)NJ_1J_1$, $N(J_1)C(=NJ_1)NJ_1J_2$, $C(=NJ_1)NJ_1J_2$, $C(=NJ_1)J_1$, $S(O)J_1$, $S(O)_2J_1$, $S(O)_2NJ_1J_2$, $N(J_1)S(O)_2J_1$, $N(J_1)(CH_2)_{nm}-OJ_1$, $N(J_1)(CH_2)_{nm}NJ_1J_2$, a conjugate group, a reporter group, $C_5$-$C_{20}$ aryl, substituted $C_5$-$C_{20}$ aryl, alicyclyl, substituted alicyclyl, heteroaryl, substituted heteroaryl, a heterocycle radical, a substituted heterocycle radical or a substituted or unsubstituted mono or poly cyclic structure that can be unsaturated, partially saturated or fully saturated and can include one or more heteroatoms selected from O, N and S, wherein said mono or poly cyclic structure is bonded directly or through said substituent group; and wherein each of said $Q_2$ can be further mono or poly substituted with one or more substituent groups.

j is 0 or 1;

jj is from 1 to about 4;

wherein each of said substituted groups are mono or poly substituted with substituent groups independently selected from halogen, trifluoromethyl, trifluoroalkoxy, $NHNH_2$, $ONH_2$, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $OJ_1$, $NJ_1J_2$, $N_3=NJ_1$, $C(=O)OJ_3$, $C(=O)J_3$, $=O$, CN, $NO_2$, $SJ_1$, $C(=O)NJ_1J_2$, $N(J_1)C(=O)J_3$, $OC(=O)NJ_1J_2$, $N(J_1)C(=O)OJ_1$, $N(J_1)C(=O)NJ_1J_2$, $N(J_1)C(S)NJ_1J_1$, $N(J_1)C(=NJ_1)NJ_1J_2$, $C(=NJ_1)NJ_1J_2$, $J_1C(=NJ_1)J_1$, $S(O)J_1$, $S(O)_2J_1$, $S(O)_2NJ_1J_2$, $N(J_1)S(O)_2J_1N(J_1)$-$(CH_2)_{nm}-OJ_1$, $N(J_1)$-$(CH_2)_{nm}-NJ_1J_2$, a conjugate group, a reporter group, a metal coordination group, an amino acid side chain, a carbohydrate, a drug, or a group capable of hydrogen bonding, $C_5$-$C_{20}$ aryl, substituted $C_5$-$C_{20}$ aryl, $C_5$-$C_{20}$ alicyclic, substituted $C_5$-$C_{20}$ alicyclic, heteroaryl, substituted heteroaryl, a heterocycle radical, a substituted heterocycle radical or a substituted or unsubstituted, linked, fused or mixed, mono or poly cyclic structure that can be unsaturated, partially saturated or fully saturated and can include one or more heteroatoms selected from O, N and S, wherein said mono or poly cyclic structure is bonded directly or through said substituent group;

each $J_1$ and $J_2$ is, independently, H, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, $C(=O)J_3$, a protecting group, an optionally linked conjugate group or a substituent group;

each $J_3$ is, independently, H, hydroxyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, a protecting group, an optionally linked conjugate group or a substituent group; and mn is from 1 to about 8.

The present invention also provides stereochemically pure compounds having the configuration:

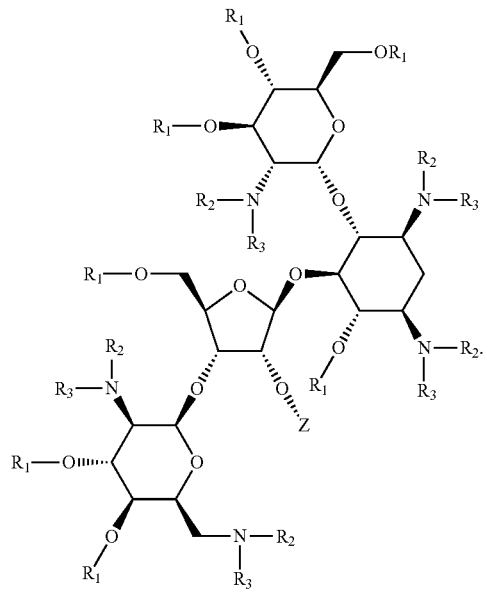

The compounds of the present invention have been shown to have in vitro and in vivo activity against selected bacteria and therefore will have utility for use in therapy.

Compounds of the invention may be prepared according to established synthetic organic chemistry techniques. In a particular general method, paromomycin is selectively protected such that the 2"-hydroxyl can be selectively functionalized. In a preferred embodiment, an allyl group is introduced and then further derivatized in a number of established ways. A particularly useful method is to convert the allyl group to an aldehyde, then introduce an amine functionality via a reductive alkylation.

In a preferred embodiment the compounds of the present invention are prepared from Paromomycin sulfate salt (commercially available from various sources including Sigma-Aldrich Co., et al.) The reactive groups are orthogonally protected as illustrated in the examples below to prepare compounds of the invention. The methods disclosed herein are amenable to a wide variety of chemical reactions to prepare a large number of Paromomycin analogs. In some preferred embodiments of the present invention each $R_1$, $R_2$ and $R_3$ is H and $R_4$ is substituted with a variety of functional groups including conjugate groups. The present invention therefor provides a variety of 2"-substituted Paromomycin analogs that are as therapeutic and/or prophylactic agents as well as processes and intermediates for making them.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups (see substituent group list below).

The term "alkenyl," as used herein, refers to a straight or branched hydrocarbon chain radical containing up to twenty four carbon atoms having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl or amino portions of the aminoalkyl group can be further substituted with substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines, for example. Aliphatic groups as used herein may optionally include further substituent groups.

The term "alicyclic" refers to a cyclic ring system wherein the ring is aliphatic. The ring system can comprise one or more rings and wherein at least one ring is aliphatic. Alicyclics include rings having any degree of saturation. Preferred alicyclics include rings having from about 5 to about 9 carbon atoms in the ring. Alicyclic as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The term "heterocyclic," or "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined, attached to a parent molecule via an alkyl group. Examples include, but are not limited to, pyridinylmethyl, pyrimidinylethyl and the like. Heteroarylalkyl groups as used herein may optionally include further substituent groups.

The term "mono or poly cyclic structure" as used in the present invention includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, hetero-aromatic, heteroarylalkyl. Such mono or poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom or through a substituent group.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "chemical functional group" as used herein, refers one or more groups that are directly attached or linked to a site in a compound. Such groups can enhance the properties of the parent compound to provide for example enhanced activity against one or more selected targets. A representative list of chemical functional groups includes, but is not limited to, H, $C_1$-$C_{20}$ alkyl; substituted alkyl; $C_2$-$C_{20}$ alkenyl; substituted alkenyl; $C_2$-$C_{20}$ alkynyl; substituted alkynyl; $C_4$-$C_7$ carbocyclic alkyl; substituted carbocyclic alkyl; alkenyl carbocyclic; substituted alkenyl carbocyclic; alkynyl carbocyclic; substituted alkynyl carbocyclic; $C_5$-$C_{14}$ aryl; substituted $C_5$-$C_{14}$ aryl; O-aralkyl, S-aralkyl, NH-aralkyl, heteroaryl; substituted heteroaryl; a heterocycle containing one or more heteroatoms selected from N, O and S; a substituted heterocycle; alicyclyl, substituted alicyclyl, a substituted or unsubstituted mono or poly cyclic structure that can be unsaturated, partially saturated or fully saturated and can include one or more heteroatoms selected from O, N and S, wherein said mono or poly cyclic structure is bonded directly or through said substituent group; hydroxyl, alkoxy, thiol, thioalkyl, halogen, an ether having 2 to 10 carbon atoms and 1 to 4 oxygen or sulfur atoms, a metal coordination group, a conjugate group, trifluoromethyl, trifluoromethoxy, $OJ_1$, $C(=O)J_3$, $=O$, $C(=O)OJ_3$, $NJ_1J_2$, $=NJ_1$, $N(J_1)C(=O)J_3$, $N(J_1)C(=O)NJ_1J_2$, $N(J_1)C(S)NJ_1J_1$, $N(J_1)S—(O)_2J_1$, $N(J_1)C(=NJ_1)NJ_1J_2$, $N(J_1)(CH_2)_{nm}OJ_1$, $N(J_1)(CH_2)_{nm}NJ_1J_2$, $C(=O)NJ_1J_2$, $OC(=O)NJ_1J_2$, $C(=NJ_1)NJ_1J_2$, $C(=NJ_1)J_1$, glutamyl ($J_1OOCCH(NJ_1J_2)$ $(CH_2)_2C(=O)$, CN, $NO_2$, $N_3$, $NHNH_2$, $ONH_2$, $S(O)J_1$, $S(O)_2NJ_1J_2$, $S(O)_2J_1$, S, $SJ_1$, silyl, an amino acid side chain, a carbohydrate, a drug, or a group capable of hydrogen bonding where mn is from 1 to about 8.

Wherein each $J_1$ and $J_2$ is, independently, H, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, $C(O)J_3$, a protecting group or an optionally linked conjugate group.

Wherein each $J_3$ is, independently, H, hydroxyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, a heterocycle radical, a substituted heterocycle radical, heteroaryl, substituted heteroaryl, $C_1$-$C_{12}$ aminoalkyl, substituted $C_1$-$C_{12}$ aminoalkyl, a protecting group or an optionally linked conjugate group.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to the parent compound. Such groups include without limitation, halogen, hydroxyl, alkyl, alkenyl, alkynyl, acyl (—C(O)$R_a$), carboxyl (—C(O)O—$R_a$), aliphatic, alicyclic, alkoxy, substituted oxo (—O—$R_a$), aryl, aralkyl, heterocyclic, heteroaryl, heteroarylalkyl, amino (—$NR_bR_c$), imino(=$NR_b$), amido (—C(O)$NR_bR_c$ or —N($R_b$)C(O)$R_a$), azido (—$N_3$), nitro (—$NO_2$), cyano (—CN), carbamido (—OC(O)$NR_bR_c$ or —N($R_b$)C(O)O$R_a$), ureido (—N($R_b$)C(O)$NR_bR_c$), thioureido (—N($R_b$)C(S)$NR_bR_c$), guanidinyl (—N($R_b$)C(=$NR_b$)$NR_bR_c$), amidinyl (—C(=$NR_b$)—$NR_bR_c$ or —N($R_b$)C($NR_b$)$R_a$), thiol (—$SR_b$), sulfinyl (—S(O)$R_b$), sulfonyl (—S(O)$_2R_b$), sulfonamidyl (—S(O)$_2NR_bR_c$ or —N($R_b$)S(O)$_2R_b$) and conjugate groups. Wherein each $R_a$, $R_b$ and $R_c$ is a further substituent group with a preferred list including without limitation alkyl, alkenyl, alkynyl, aliphatic, alkoxy, acyl, aryl, aralkyl, heteroaryl, alicyclic, heterocyclic and heteroarylalkyl.

In one aspect of the present invention the properties of aminoglycosides having formula I are modified by covalent attachment of one or more conjugate groups that modify one or more properties including but not limited to pharmacodynamic, pharmacokinetic, binding, absorption, cellular distribution, cellular uptake, charge and clearance. Conjugate groups are routinely used in the chemical arts with a preferred list including without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

Reporter groups that are suitable as conjugate moieties include any moiety that can be detected by, for example, spectroscopic means. Examples of reporter groups include dyes, fluorophores, phosphors, radiolabels, and the like. In some embodiments, the reporter group is biotin, flourescein, rhodamine, coumarin, or related compounds. Reporter groups can also be attached to other conjugate moieties.

Conjugate moieties can be attached directly to a compound of the present invention or through a linking moiety (linker or tether). Linkers are bifunctional moieties that serve to covalently connect a conjugate moiety to a desired position of another compound. In some embodiments, the linker comprises a chain structure or an oligomer of repeating units such as ethylene glyol or amino acid units. The linker can have at least two functionalities, one for attaching to the desired compound and the other for attaching to the conjugate moiety. Example linker functionalities can be electrophilic for reacting with nucleophilic groups or nucleophilic for reacting with electrophilic groups. In some embodiments, linker functionalities include amino, hydroxyl, carboxylic acid, thiol, unsaturations (e.g., double or triple bonds), and the like. Some example linkers include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA).

The term "protecting group," as used herein, refers to a labile chemical moiety which is known in the art to protect reactive groups including without limitation, hydroxyl, amino and thiol groups, against undesired reactions during synthetic procedures.

Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Chemical functional groups can also be "blocked" by including them in a precursor form. Thus, an azido group can be used considered as a "blocked" form of an amine since the azido group is easily converted to the amine. Further representative protecting groups utilized in oligonucleotide synthesis are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Examples of amino protecting groups include, but are not limited to, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

The synthesized compounds can be separated from a reaction mixture and further purified by a method such as column chromatography, high pressure liquid chromatography, or recrystallization. Further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and transisomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus, Brucella* and other organisms.

It has been found that the compounds of the present invention possess antibacterial activity against a wide spectrum of gram positive and gram negative bacteria, as well as enterobacteria and anaerobes. The compounds, by reason of their in vitro activity, may be used in scrub solutions for surface inhibition of bacterial growth e.g. in sterilization of glasswear or as an additive in fabric laundering compositions.

Accordingly there is provided a method of treating bacterial infection in a mammal comprising administering to the mammal, for example a human, an effective amount of a compound of the invention. By "effective amount" is meant an amount of compound which upon administration is capable of reducing or preventing proliferation of the bacteria or reducing or preventing symptoms associated with the bacterial infection. The actual amount of compound administered and the route of administration will depend upon the particular disease or bacteria as well as other factors such as the size, age, sex and ethnic origin of the individual being treated and is determined by routine analysis. The compounds of the invention may also be formulated into compositions together with pharmaceutically acceptable carriers for parenteral injection, for oral administration in solid or liquid form, for rectal administration, and the like. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants, etc. As are routine in the formulation art. Compositions of the invention may also include additional active ingredients. Dosage forms include solutions, powders, tables, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carries include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances of binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et. al., Chapter 89; and Longer et. al., Chapter 91 In: Remington's Pharmaceutical Sciences, 18$^{th}$ Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); filters (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods will known in the art. The preparations may be also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided soled carriers or both, and then, if necessary, shaping the product.

Formulations of the present invention suitable for oral administration may be presented as discrete units such as capsules, cachets or tables each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

Included within the scope of the present invention are the pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts.

EXAMPLES

Example 1

4',6'-O-Benzylidene-penta-N-benzyloxycarbonyl paromomycin (2)

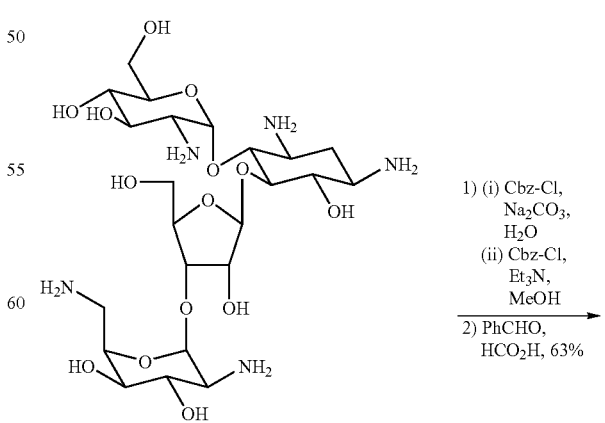

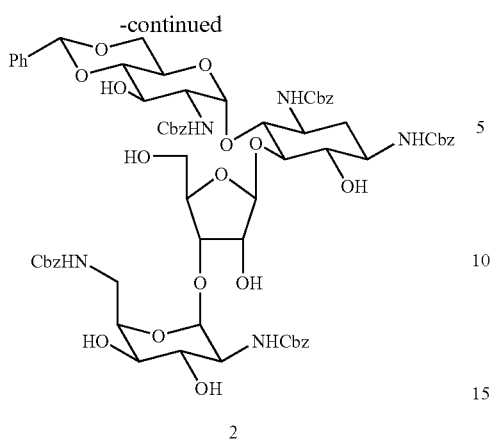

2

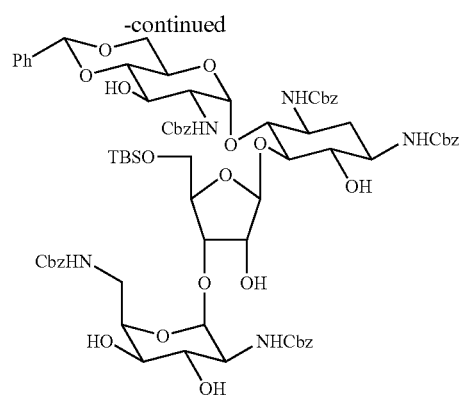

3

Sodium carbonate (55.0 g, 0.523 mol) and Cbz-Cl (20.00 mL, 0.139 mol) were added to paromomycin sulfate (30.00 g, 0.0271 mol) in water (500 mL). After 35 hours under vigorous stirring, the water was decanted and the white precipitate was washed with water twice. A solution of triethylamine (97.00 mL, 0.697 mol) in methanol (600 mL) was added, followed by Cbz-Cl (25.00 mL, 0.174 mol). After 24 hours, dimethylamine (100 mL of a 40% aqueous solution) was added to quench the remaining Cbz-Cl. The solvents were evaporated and the oil was washed with 3% methanol in ether twice and water. The resulting sticky solid was co distilled with pyridine (200 mL) three times and at ½ of the volume of the third co distillation, toluene (200 mL) was added and the solvents were evaporated to dryness. Another co-distillation with toluene (300 mL) was done before heating the flask at 60° C. under 10 mm Hg vacuum for 12 hours. Freshly distilled benzaldehyde (400 mL) was added to the resulting white solid and sonication was used to form a solution. To the stirred mixture was added 4 angstrom molecular sieves (15 g) and formic acid (20.00 mL, 0.530 mol). After stirring for 12 hours at room temperature, the mixture was added dropwise to a stirred ice-cold solution of saturated aqueous $Na_2CO_3$, extracted with ethyl acetate (3 times), and the organic layer was washed with water, brine and dried over $Na_2SO_4$. The solvent was evaporated to dryness and excess benzaldehyde was removed under vacuum to afford a crude solid, which was purified by flash column chromatography over silica gel (3% MeOH/$CH_2Cl_2$) to obtain pure compound 2 (23.89 g, 63%).

The spectroscopic analysis of the resulting material was consistent with data reported in the literature for the identical material (Hanessian S., Takamoto T., Masse R., Patil G.; Aminoglycoside antibiotics: Chemical conversion of neomycin B, paromomycin, and lividomycin B into bioactive pseudosaccharides; *Can. J. Chem.*, 1978, 56, 1482).

Example 2

4',6'-O-Benzylidene-penta-N-benzyloxycarbonyl-5''-O-tertbutyldimethylsilyl paromomycin (3)

The alcohol 2 (6.00 g, 4.367 mmol) dried by two co distillations with toluene was dissolved in $CH_2Cl_2$ (400 mL) and 2,4,6-collidine (1.15 mL, 8.735 mmol) followed by TBDM-SOTf (0.50 mL, 2.184 mmol) were added at 0° C. After 18 hours, 0.6 equivalent of TBDMSOTf was added and 6 hours later, some of the $CH_2Cl_2$ was evaporated to a smaller volume for washing with HCl (0.5 M) twice and $H_2O$. Drying with $Na_2SO_4$ and purification by silica gel chromatography (2% MeOH/$CH_2Cl_2$) gave 3 (4.861 g, 75%). $[\alpha]_D$+41.8° (c 0.9, $CHCl_3$); $R_f$ 0.6 ($CHCl_3$:EtOAc:MeOH (20:5:3); $^1$H NMR (300 MHz, $CDCl_3$) δ7.60-7.10 (m, 30H), 5.60-3.00 (m, 41H), 2.20 (m, 1H), 1.30 (m, 1H), 0.83 (s, 9H), 0.01 (s, 6H); ESI m/z calcd $C_{76}H_{93}N_5O_{24}Si$ 1487.60 found 1488.9.

Example 3

2''-O-Allyl-4,6'-O-benzylidene-penta-N-benzyloxycarbonyl-5''-O-tertbutyldimethylsilyl paromomycin (4)

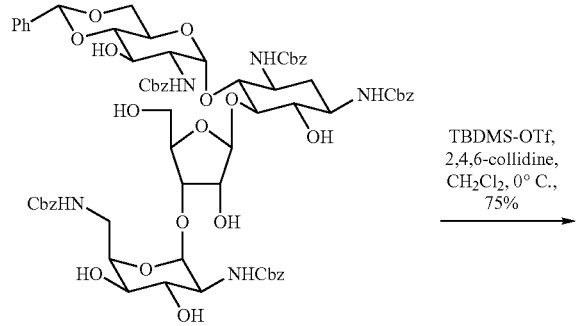

2

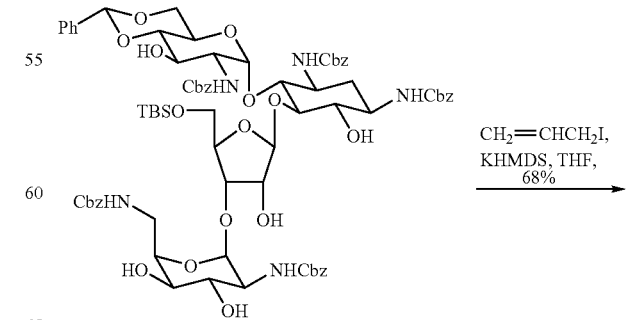

3

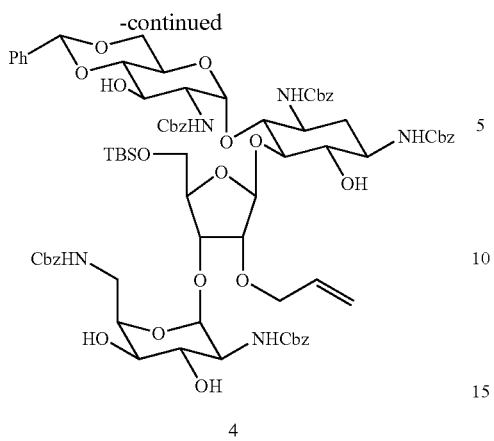

4

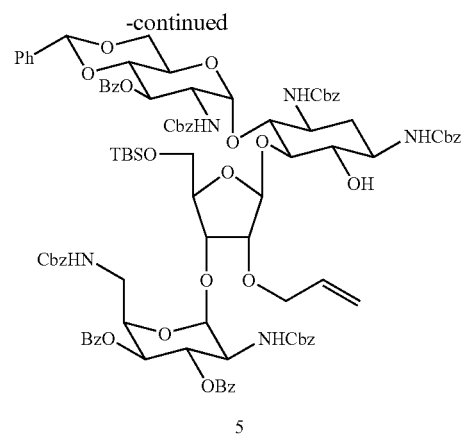

5

Compound 3 (2.10 g, 1.411 mmol) was co-distilled with toluene twice and the residue dissolved in dry THF (70 mL) in a flask covered with aluminum foil. Allyl iodide (1.29 mL, 14.11 mmol) was added followed by the dropwise addition of 0.5 M KHMDS solution in toluene (1.411 mL, 0.706 mmol). The mixture was stirred for overnight at room temperature, then, 0.3 equivalents of KHMDS was added and 6 hours later the reaction mixture was quenched with an aqueous solution of NH$_4$Cl satd. (2 mL) and water. THF was evaporated and the aqueous layer was extracted with ethyl acetate (3 times), and the organic layer was washed with a sodium thiosulfate solution, brine and dried over Na$_2$SO$_4$. The solvent was evaporated to dryness to afford a crude solid, which was purified by silica gel flash chromatography (1.5% MeOH/CH$_2$Cl$_2$) providing the corresponding allyl ether 4 (1.468 g, 68%).

$[\alpha]_D$+22.2° (c 2.6, CHCl$_3$); R$_f$ 0.7 (CHCl$_3$:EtOAc:MeOH (20:5:3); $^1$H NMR (300 MHz, CDCl$_3$) δ7.60-7.10 (m, 30H), 6.30-3.00 (m, 44H), 2.20 (m, 1H), 1.30 (m, 1H), 0.83 (s, 9H), 0.01 (s, 6H); $^{13}$C NMR (75 MHz, CDCl$_3$) δ 157.7, 157.1, 156.5, 155.6, 137.2, 136.2, 135.7, 128.8, 128.5, 128.4, 128.0, 127.9, 127.4, 126.3, 126.0, 101.5, 99.4, 85.2, 82.3, 81.4, 77.2, 76.9, 76.6, 76.2, 74.2, 72.7, 69.5, 68.5, 67.3, 66.7, 63.5, 62.8, 56.5, 52.7, 50.8, 40.1, 33.7, 25.8, 18.1, 14.1, −5.3, −5.5, −5.8; ESI m/z calcd for C$_{79}$H$_{97}$N$_5$O$_{24}$Si 1527.63, found 1528.8.

A solution containing 4 (5.30 g, 3.46 mmol) and N,N-dimethyl-4-aminopyridine (100 mg) in dry pyridine (100 mL) was treated with benzoyl chloride (3.017 mL, 34.641 mmol). The reaction mixture was stirred at room temperature for 36 hours water (5 mL) was added and after standing for 10 min, the solvent was removed under vacuum. The residue was dissolved in ethyl acetate, and the organic layer was washed with NaHCO$_3$ satd., 0.5 M HCl and water, dried over Na$_2$SO$_4$ and concentrated under vacuum. The crude product was purified by silica gel flash chromatography (1:1 EtOAc/hexane) to yield compound 5 (5.3 g, quant.).

$[\alpha]_D$+11.6° (c 2.5, CHCl$_3$); R$_f$ 0.6 (1:1 EtOAc/hexane); $^1$H NMR (300 MHz, CDCl$_3$) δ 8.10-7.10 (m, 47H), 6.30-3.00 (m, 44H), 2.20 (m, 1H), 1.30 (m, 1H), 0.83 (s, 9H), 0.01 (s, 6H); $^{13}$C NMR (75 MHz, CDCl$_3$) δ158.5, 156.4, 138.0, 137.0, 136.9, 136.8, 136.5, 129.6, 129.5, 129.4, 129.2, 129.1, 129.0, 128.8, 128.7, 128.4, 128.3, 128.2, 128.1, 127.0, 98.5, 82.2, 78.1, 70.3, 70.2, 68.0, 67.8, 67.6, 67.4, 67.2, 26.6, 18.9; ESI m/z calcd for C$_{100}$H$_{109}$N$_5$O$_{27}$Si 1839.71 found 1840.9.

Example 4

2"—O-Allyl-3', 3''',4'''-tri-O-benzoyl-4',6'-O-benzylidene-penta-N-benzyloxycarbonyl-5"-O-tertbutyldimethylsilyl paromomycin (5)

Example 5

3', 3''',4'''-Tri-O-benzoyl-4',6'-O-benzylidene-penta-N-benzyloxycarbonyl-2"-O-methylenecarbonyl-5"-O-tertbutyldimethylsilyl paromomycin (6)

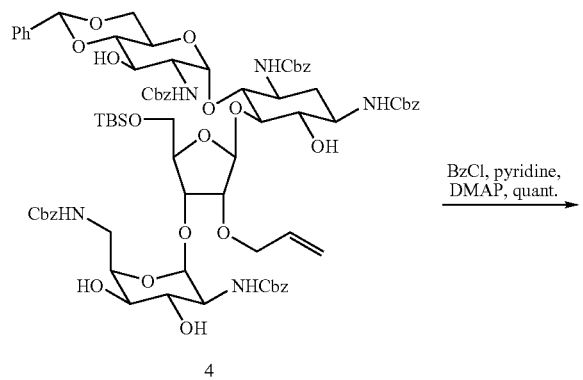

4

BzCl, pyridine,
DMAP, quant.
⟶

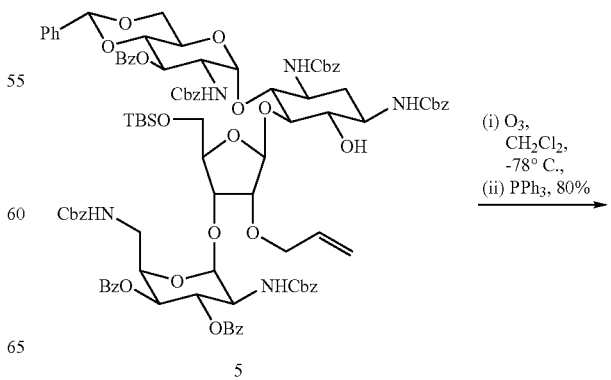

5

(i) O$_3$,
CH$_2$Cl$_2$,
−78° C.,
(ii) PPh$_3$, 80%
⟶

-continued

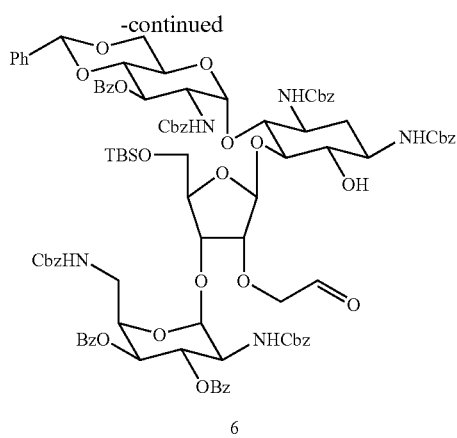

6

The allyl ether derivative 5 (2.00 g, 1.086 mmol) in $CH_2Cl_2$ (60 mL) was cooled at −78° C. and ozone was bubbled for 2 hours after which excess ozone was removed by bubbling argon. The mixture was treated with $PPh_3$ (427 mg, 1.629 mmol), warmed to room temperature and the solvent was removed under vacuum. The crude solid was purified by silica gel flash chromatography (2:3 EtOAc/hexane) to give the aldehyde 6 (1.627 g, 80%).

$R_f$ 0.4 (1:1 EtOAc/hexane); ESI m/z $C_{99}H_{107}N_5O_{28}Si$ 1841.69, found 1842.9.

Example 6

General Procedure for Reductive Amination

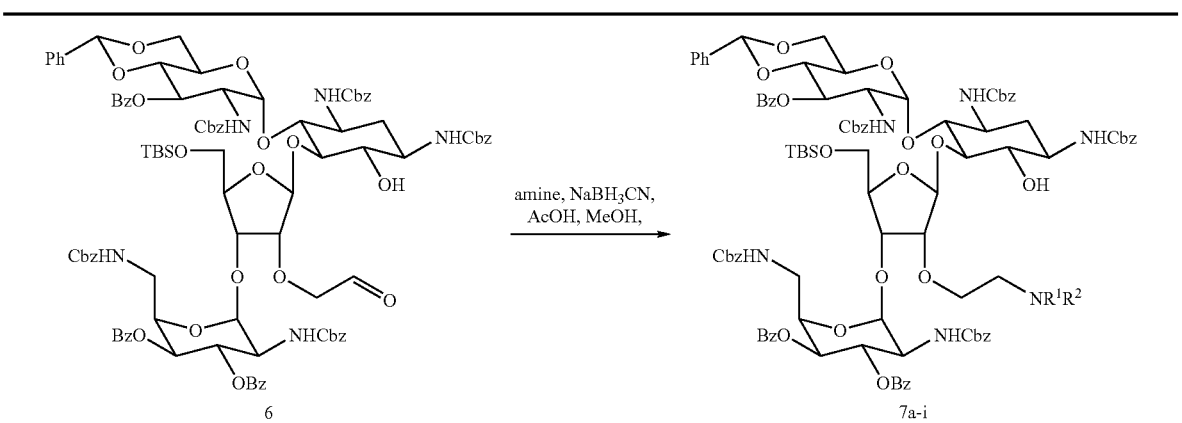

| Compound | R¹ | R² |
|---|---|---|
| 7a | H | 3-pyridyl |
| 7b | H | 3-pyridylmethyl |
| 7c | H | propyl-NHCbz |
| 7d | H | ethyl-NHCbz |
| 7e | H | benzimidazol-2-ylmethyl |

-continued
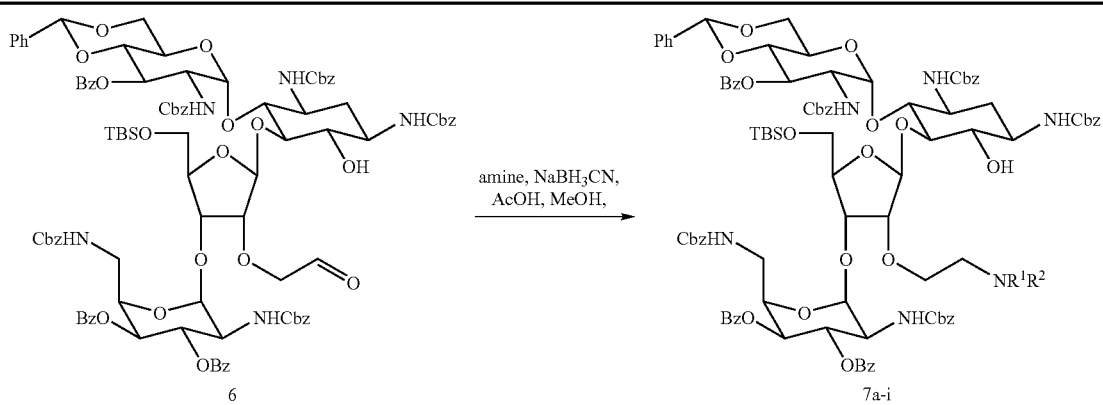
| Compound | R¹ | R² |
| --- | --- | --- |
| 7f | H | 4-methylbenzyl |
| 7g | Me | Me |
| 7h | -CH₂CH₂-NHCbz | -CH₂CH₂-NHCbz |
| 7i | (R¹ and R² together form a ring with NCbz) | |
| 7l | H | phenyl |
| 7m | H | quinolin-3-yl |
| 7n | H | cyclohexyl |
| 7o | H | 2-(pyridin-3-yl)ethyl |
| 7p | H | 2-phenylethyl |

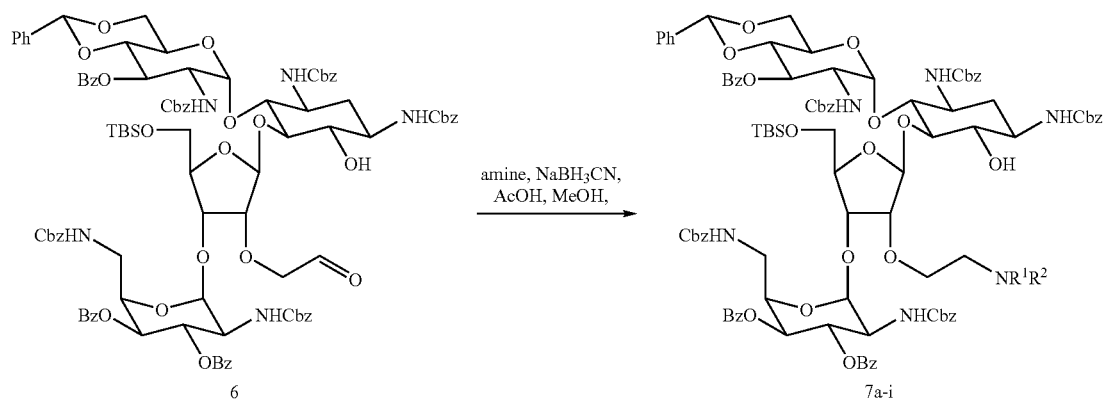
| Compound | R¹ | R² |
|---|---|---|
| 7q | H | benzyl |
| 7r | H | 3-hydroxybenzyl |
| 7s | H | (2-NHBoc-pyridin-5-yl)methyl |
| 7t | H | (2-NHBoc-pyridin-4-yl)methyl |
| 7u | H | pyridin-2-yl-methyl |
| 7v | H | 3,3-dimethylbutyl |
| 7w | H | 3-hydroxyadamantyl |
| 7x | H | 3-phenylpropyl |

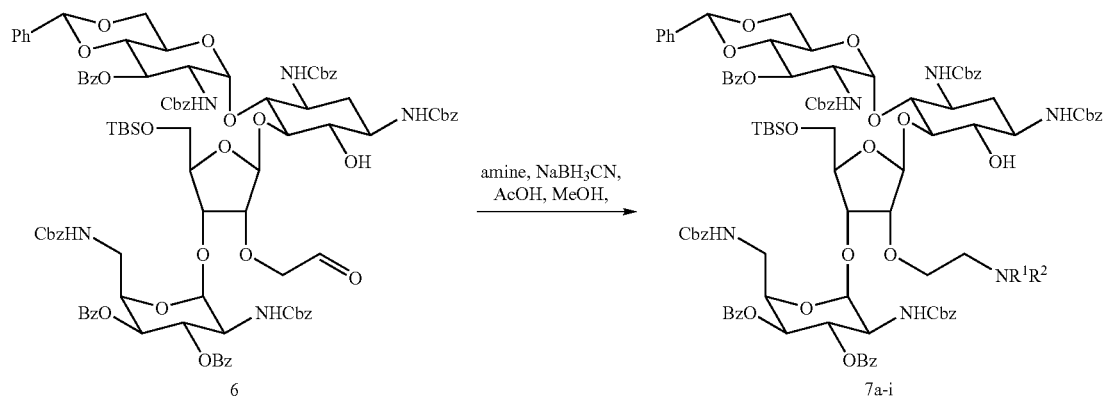
| Compound | R[1] | R[2] |
|---|---|---|
| 7y | H | 3,5-dimethoxyphenethyl |
| 7z | H | 4-phenylbutyl |
| 7aa | H | 4-biphenylethyl |
| 7ab | H | 2-(norbornyl)ethyl |
| 7ac | H | 1,2,3,4-tetrahydronaphthalen-1-yl |
| 7ad | H | cholestanyl |

-continued
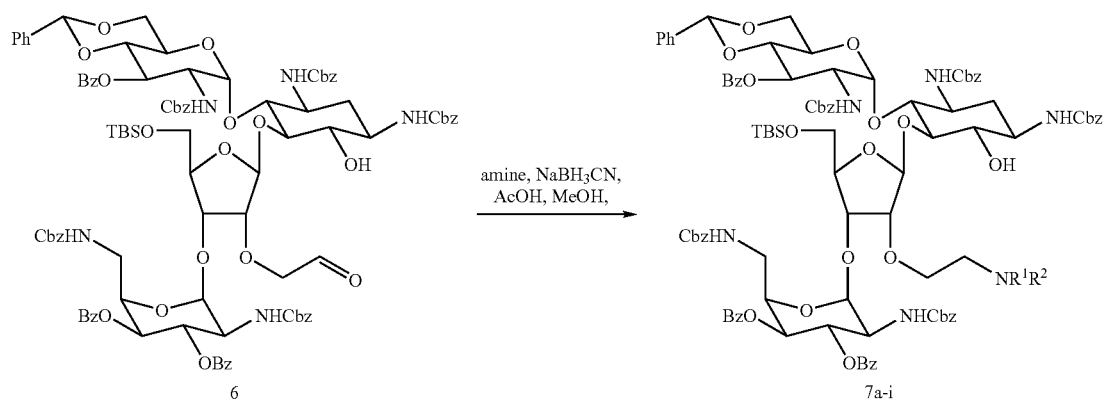
| Compound | R¹ | R² |
|---|---|---|
| 7ae | H | propyl-naphthalimide |
| 7af | H | propyl-3,5-bis(trifluoromethyl)phenyl |
| 7ag | phenethyl | 3-phenylpropyl |
| 7ah | H | 2-(4-(trifluoromethyl)phenyl)ethyl |
| 7ai | nonyl | nonyl |
| 7aj | H | 2-(4-methoxyphenyl)ethyl |

To a mixture of 6 (80.0 mg, 0.043 mmol) and appropriate amine (0.129 mmol) in dry MeOH (3 mL) was added acetic acid (0.1 mL) followed by NaBH$_3$CN (1.0 M in THF, 60 μL). The mixture was stirred at room temperature overnight. The solvents were removed under vacuum and the crude solid was dissolved in ethyl acetate and washed with a solution of NaHCO$_3$ satd. and dried over Na$_2$SO$_4$. After evaporation of the solvents, the residue was purified by flash chromatography.

Compound 7a. 90% yield from 2-aminopyridine and compound 6 using the general procedure above; silica gel flash chromatography eluent:EtOAc:hexane (4:1); $[\alpha]_D$+15.7° (c 1.3, CHCl$_3$); R$_f$ 0.5 (EtOAc); ESI m/z C$_{104}$H$_{113}$N$_7$O$_{27}$Si 1919.75, found 1920.8;

Compound 7b. 90% yield from 2-(aminomethyl)pyridine and compound 6 using the general procedure above; silica gel flash chromatography eluent: 3% MeOH/CH$_2$Cl$_2$; $[\alpha]_D$+17.8° (c 0.9, CHCl$_3$); R$_f$ 0.6 (5% MeOH/CH$_2$Cl$_2$); ESI m/z C$_{105}$H$_{115}$N$_7$O$_{27}$Si 1933.76, found 1934.8;

Compound 7c. 90% yield from N-1-(benzyloxycarbonyl)-1,3-diaminopropane and compound 6 using the general procedure above; silica gel flash chromatography eluent: 3% MeOH/CH$_2$Cl$_2$; $[\alpha]_D$+12.7° (c 0.8, CHCl$_3$); R$_f$ 0.5 (5% MeOH/CH$_2$Cl$_2$); FAB m/z C$_{110}$H$_{123}$N$_7$O$_{29}$Si 2033.81, found 2036.1.

Compound 7d. 90% yield from N-1-(benzyloxycarbonyl)-1,2-diaminoethane and compound 6 using the general procedure above; silica gel flash chromatography eluent: 3% MeOH/CH$_2$Cl$_2$; $[\alpha]_D$+21.6.7° (c 1.7, CHCl$_3$); R$_f$ 0.5 (5% MeOH/CH$_2$Cl$_2$); ESI m/z C$_{109}$H$_{121}$N$_7$O$_{29}$Si 2019.80, found 2021.9;

Compound 7e. 90% yield from 2-aminomethylbenzimidazole and compound 6 using the general procedure above (note: the benzylidene and the TBS were often removed during the reductive amination); silica gel flash chromatography eluent: 7% MeOH/CH$_2$Cl$_2$; $[\alpha]_D$+11.5° (c 1.1, CHCl$_3$); R$_f$ 0.5 (10% MeOH/CH$_2$Cl$_2$); ESI m/z C$_{94}$H$_{98}$N$_8$O$_{27}$ 1770.65, found 1771.7;

Compound 7f. 90% yield from p-methylbenzylamine and compound 6 using the general procedure above; silica gel flash chromatography eluent: 3% MeOH/CH$_2$Cl$_2$; $[\alpha]_D$+8.9° (c 1.7, CHCl$_3$); R$_f$ 0.6 (5% MeOH/CH$_2$Cl$_2$); ESI m/z C$_{107}$H$_{118}$N$_6$O$_{27}$Si 1946.78, found 1947.5.

Compound 7g. 90% yield from dimethylamine and compound 6 using the general procedure above; silica gel flash chromatography eluent: 3% MeOH/CH$_2$Cl$_2$; $[\alpha]_D$+28.3° (c 0.8, CHCl$_3$); R$_f$ 0.6 (10% MeOH/CH$_2$Cl$_2$); ESI m/z C$_{101}$H$_{114}$N$_6$O$_{27}$Si 1870.75, found 1871.8;

Compound 7h 90% yield from bis-[N-1-(benzyloxycarbonyl)aminoethyl]amine and compound 6 using the general procedure above; silica gel flash chromatography eluent: 3% MeOH/CH$_2$Cl$_2$; $[\alpha]_D$+10.8° (c 1.5, CHCl$_3$); R$_f$ 0.7 (5% MeOH/CH$_2$Cl$_2$); ESI m/z C$_{102}$H$_{116}$N$_8$O$_{33}$ 1980.76, found 1981.7;

Compound 7i. 90% yield from N-1-(benzyloxycarbonyl) piperazine and compound 6 using the general procedure above; silica gel flash chromatography eluent: 3% MeOH/CH$_2$Cl$_2$; $[\alpha]$D+13.1° (c 1.2, CHCl$_3$); R$_f$ 0.5 (5% MeOH/CH$_2$Cl$_2$); FAB m/z C$_{118}$H$_{128}$N$_7$O$_{30}$Si 2150.85, found 2149.6.

Compound 7l. 88% yield from aniline and compound 6 using the general procedure above; ESI m/z C$_{105}$H$_{114}$N$_6$O$_{27}$Si 1920.14, found 1921.0; No $^1$H NMR available.

Compound 7m. 84% yield from 3-aminoquinoline and compound 6 using the general procedure above; ESI m/z C$_{108}$H$_{115}$N$_7$O$_{27}$Si 1971.18, found 1972.0

Compound 7n. 88% yield from cyclohexylamine and compound 6 using the general procedure above; ESI m/z C$_{105}$H$_{120}$N$_6$O$_{27}$Si 1926.19, found 1927.0

Compound 7o. 92% yield from 3-(2-aminoethyl)pyridine and compound 6 using the general procedure above; ESI m/z C$_{106}$H$_{117}$N$_7$O$_{27}$Si 1949.18, found 1950.3

Compound 7p. 74% yield from n-phenethylamine and compound 6 using the general procedure above; ESI m/z C$_{107}$H$_{118}$N$_6$O$_{27}$Si 1948.19, found 1949.1

Compound 7q was prepared from benzylamine and compounds 6 and was subsequently taken on directly to the next step without further characterization.

Compound 7r was prepared from 3-aminophenol and compounds 6 and was subsequently taken on directly to the next step without further characterization.

Compound 7s was prepared from N-2-(t-butoxycarbonylamino)-5-(aminomethyl)pyridine and compounds 6 and was subsequently taken on directly to the next step without further characterization.

Compound 7t was prepared from N-2-(t-butoxycarbonylamino)-4-(aminomethyl)pyridine and compounds 6 and was subsequently taken on directly to the next step without further characterization.

Compound 7u. 90% yield from 2-aminopyridine and compound 6 using the general procedure above; ESI m/z C$_{104}$H$_{113}$N$_7$O$_{27}$Si 1921.13, found 1921.0

Compound 7v was prepared from 3,3-dimethylaminopropane and compounds 6 and was subsequently taken on directly to the next step without further characterization.

Compound 7w was prepared from 1-amino-3-hydroxyadamantane and compounds 6 and was subsequently taken on directly to the next step without further characterization.

Compound 7x. 85% yield from n-phenpropylamine and compound 6 using the general procedure above; ESI m/z C$_{108}$H$_{120}$N$_6$O$_{27}$Si 1962.22, found 1963.3

Compound 7y was prepared from 1-amino-2-(2,4-dimethoxyphen-1-yl)ethane and compounds 6 and was subsequently taken on directly to the next step without further characterization.

Compound 7z was prepared from n-phenbutylamine and compound 6 and was subsequently taken on directly to the next step without further characterization.

Compound 7aa was prepared from (4-phenyl)phenethylamine and compound 6 and was subsequently taken on directly to the next step without further characterization.

Compound 7ab was prepared from 1-amino-2-(norborn-2-yl)ethane and compound 6 and was subsequently taken on directly to the next step without further characterization.

Compound 7ac was prepared from 2-aminonapthylene and compound 6 and was subsequently taken on directly to the next step without further characterization.

Compound 7ad was prepared from the amino-substituted cholesterol and compound 6 and was subsequently taken on directly to the next step without further characterization.

Compound 7ae was prepared from 2-(2-Amino-ethyl)-benzo[de]isoquinoline-1,3-dione and compounds 6 and was subsequently taken on directly to the next step without further characterization.

Compound 7af was prepared from 2-(3,5-Bis-trifluoromethyl-phenyl)-ethylamine and compound 6 and was subsequently taken on directly to the next step without further characterization.

Compound 7ag was prepared from Phenethyl-(3-phenyl-propyl)-amine and compound 6 and was subsequently taken on directly to the next step without further characterization.

Compound 7ah was prepared from 2-(4-Trifluoromethylphenyl)-ethylamine and compound 6 and was subsequently taken on directly to the next step without further characterization.

Compound 7ai was prepared from dioctylamine and compound 6 and was subsequently taken on directly to the next step without further characterization.

Compound 7aj was prepared from 2-(4-Methoxyphenyl) ethylamine and compound 6 and was subsequently taken on directly to the next step without further characterization.

Example 7

General Procedure for Debenzoylation

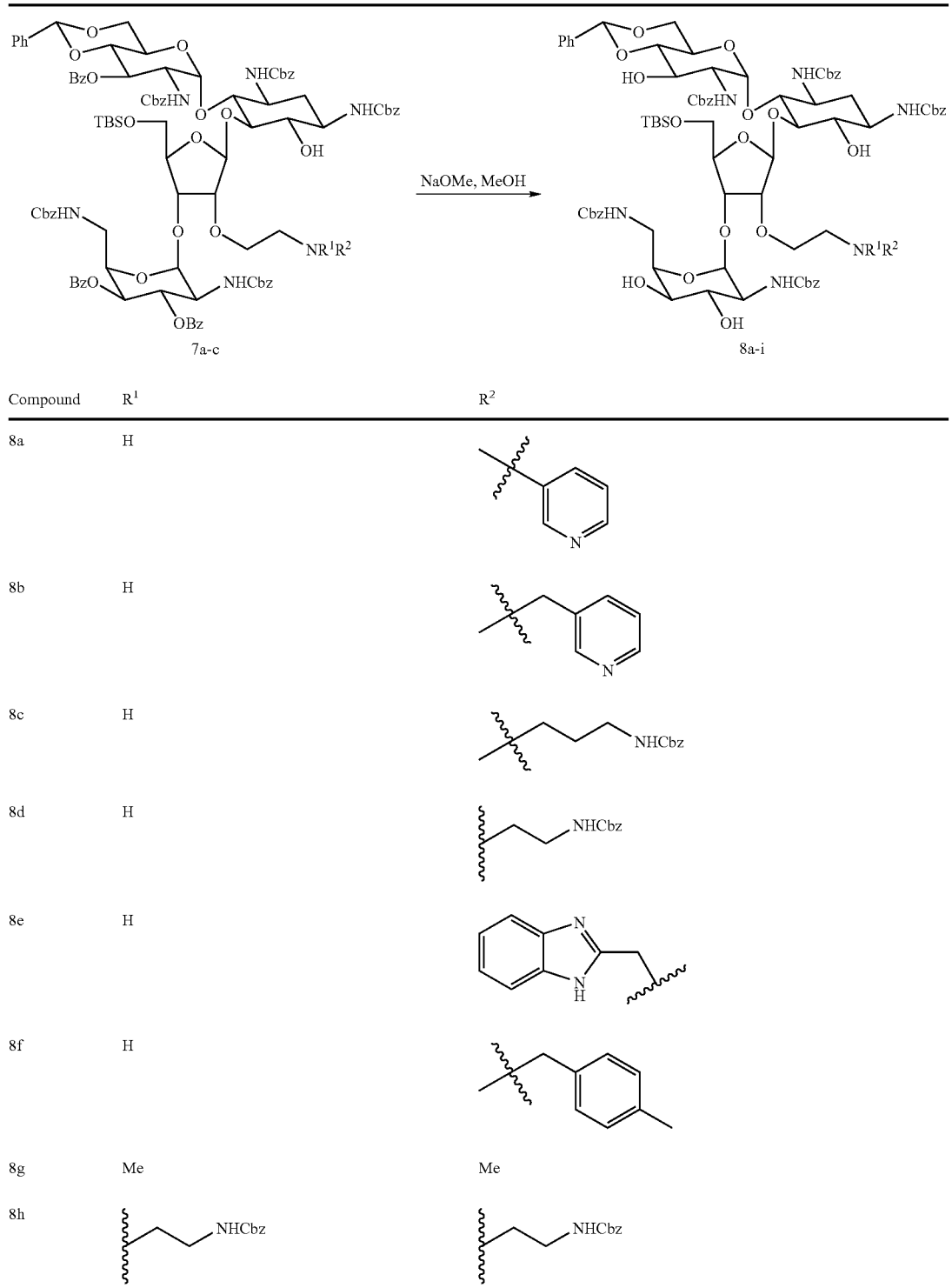

| Compound | R$^1$ | R$^2$ |
|---|---|---|
| 8a | H | 3-pyridyl |
| 8b | H | 3-pyridylmethyl |
| 8c | H | -(CH$_2$)$_3$NHCbz |
| 8d | H | -(CH$_2$)$_2$NHCbz |
| 8e | H | benzimidazol-2-ylmethyl |
| 8f | H | 4-methylbenzyl |
| 8g | Me | Me |
| 8h | -(CH$_2$)$_2$NHCbz | -(CH$_2$)$_2$NHCbz |

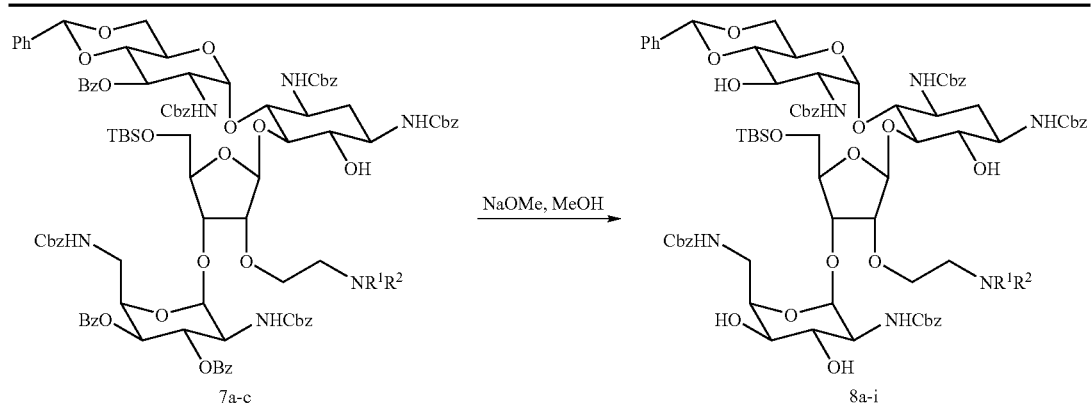
| Compound | R[1] | R[2] |
|---|---|---|
| 8i | (cycle with NCbz) | |
| 8l | H | phenyl |
| 8m | H | quinolin-3-yl |
| 8n | H | cyclohexyl |
| 8o | H | 2-(pyridin-3-yl)ethyl |
| 8p | H | 2-phenylethyl |
| 8q | H | benzyl (with methyl) |
| 8r | H | 3-hydroxyphenyl |

-continued
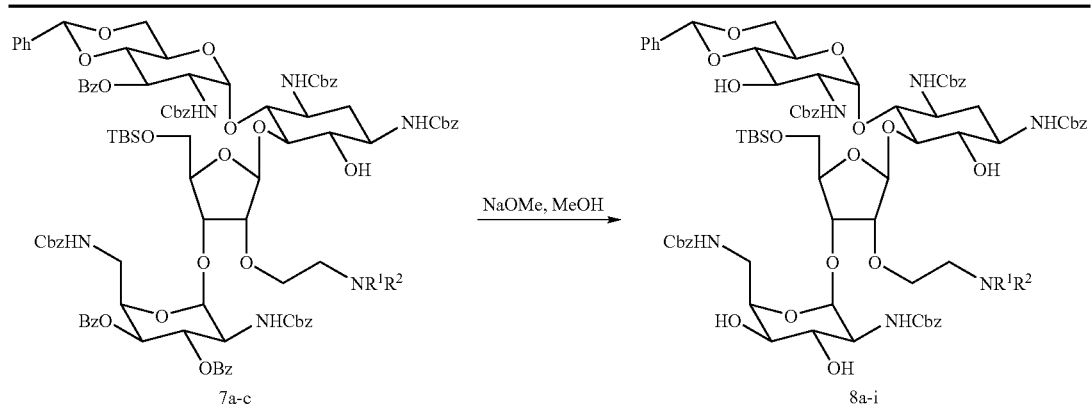
| Compound | R¹ | R² |
|---|---|---|
| 8s | H | 5-(2-NHBoc-pyridyl)methyl |
| 8t | H | 4-(2-NHBoc-pyridyl)methyl |
| 8u | H | 2-pyridyl |
| 8v | H | neopentyl-methyl (3,3-dimethylbutyl) |
| 8w | H | 3-hydroxy-1-adamantyl |
| 8x | H | 3-phenylpropyl |
| 8y | H | 2-(3,5-dimethoxyphenyl)ethyl |
| 8z | H | 4-phenylbutyl |

-continued
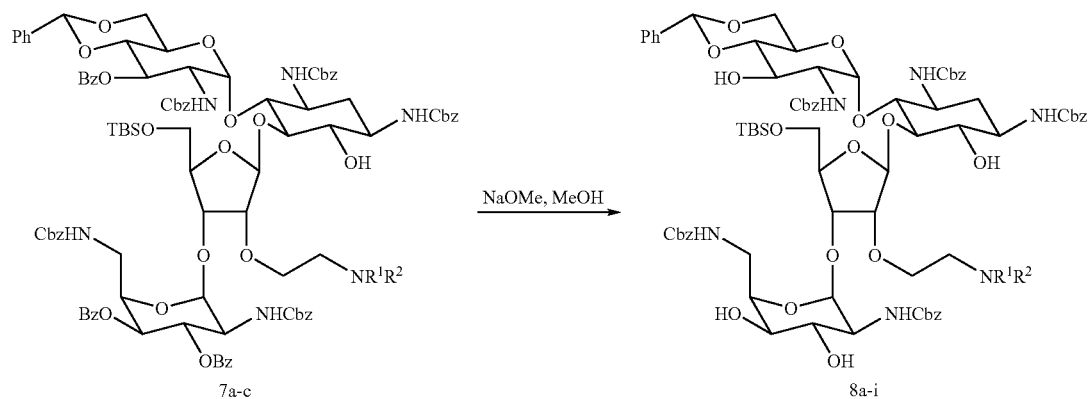
| Compound | R[1] | R[2] |
|---|---|---|
| 8aa | H | 4-biphenyl-propyl |
| 8ab | H | norbornyl-ethyl |
| 8ac | H | 1,2,3,4-tetrahydronaphthalen-1-yl |
| 8ad | H | cholestanyl |
| 8ae | H | naphthalimido-ethyl |
| 8af | H | 3,5-bis(trifluoromethyl)phenyl-propyl |

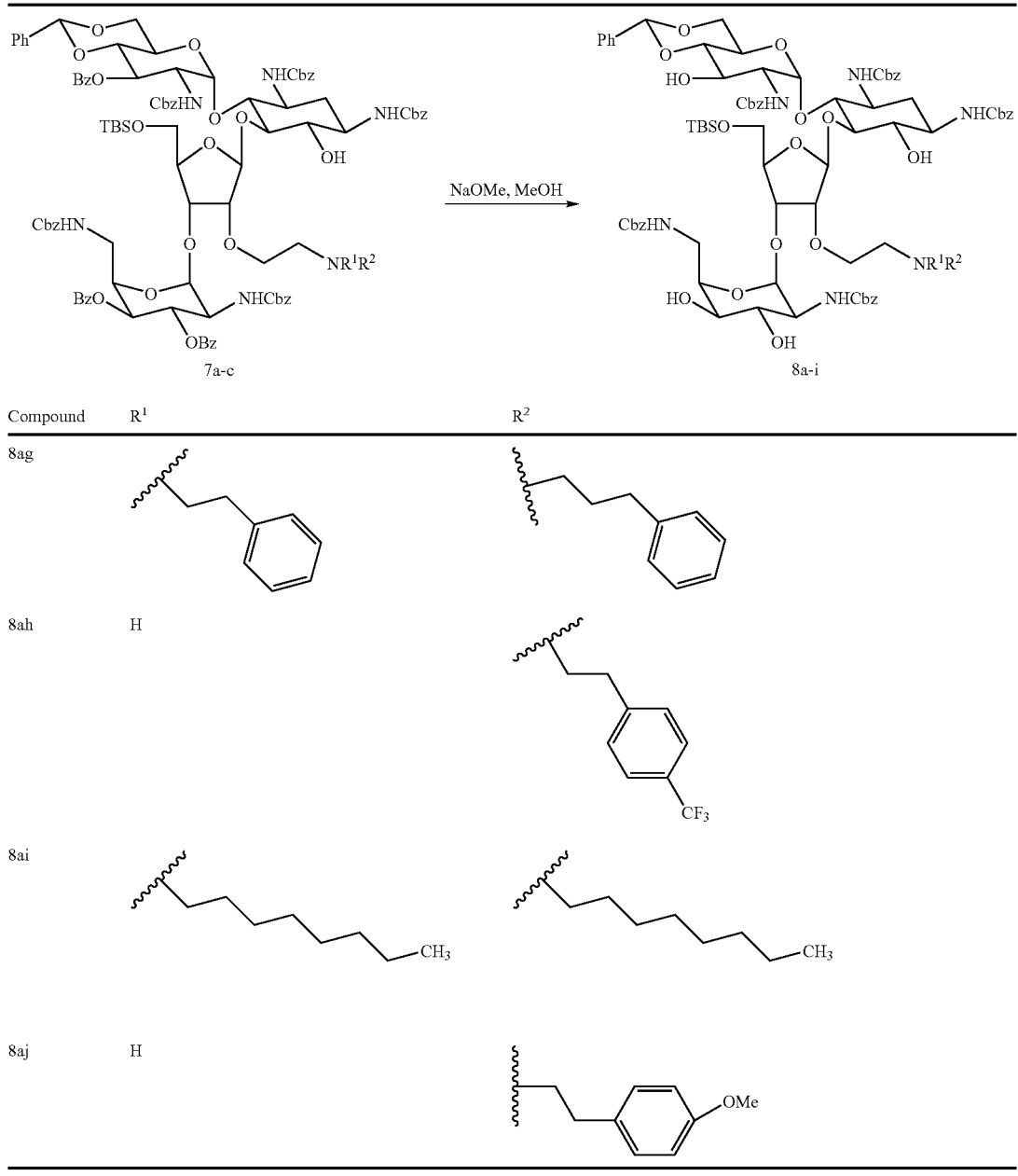

| Compound | R¹ | R² |
|---|---|---|
| 8ag | ~CH₂CH₂-Ph | ~CH₂CH₂-Ph |
| 8ah | H | ~CH₂CH₂-C₆H₄-CF₃ |
| 8ai | ~(CH₂)₈CH₃ | ~(CH₂)₈CH₃ |
| 8aj | H | ~CH₂CH₂-C₆H₄-OMe |

The ester was treated with a catalytic amount of NaOMe in MeOH (1:1, 2 mL, pH 9-10) and stirred at room temperature for overnight. The solution was cooled down to −78° C. and dry ice was added, solvent was removed under vacuum and the residue was taken in $CH_2Cl_2$ and filtered over Celite. After removal of the solvent under vacuum the solid was purified by silica gel flash chromatography.

Compound 8a. 95% yield from compound 7a following the general procedure; silica gel flash chromatography eluent: 5% MeOH/$CH_2Cl_2$; $[\alpha]_D$+8.9° (c 1.4, MeOH); $R_f$ 0.2 (5% MeOH/$CH_2Cl_2$); ESI m/z $C_{83}H_{101}N_7O_{24}Si$ 1607.67, found 1630.8 (M+Na);

Compound 8b. 95% yield from compound 7b following the general procedure; silica gel flash chromatography eluent: 5% MeOH/$CH_2Cl_2$; $[\alpha]_D$+10.3° (c 1.1, MeOH); $R_f$ 0.1 (5% MeOH/$CH_2Cl_2$); ESI m/z $C_{84}H_{103}N_7O_{24}Si$ 1621.68, found 1644.8 (M+Na);

Compound 8c. 95% yield from compound 7c following the general procedure; silica gel flash chromatography eluent: 5% MeOH/$CH_2Cl_2$; $R_f$ 0.1 (5% MeOH/$CH_2Cl_2$).

Compound 8d. 95% yield from compound 7d following the general procedure; silica gel flash chromatography eluent: 5% MeOH/$CH_2Cl_2$; $R_f$ 0.1 (5% MeOH/$CH_2Cl_2$);

Compound 8e. 95% yield from compound 7e following the general procedure (the benzylidene and the TBS were removed during the reductive amination); silica gel flash chromatography eluent: 10% MeOH/$CH_2Cl_2$; $[\alpha]_D$+7.3° (c 1.6, MeOH); $R_f$ 0.2 (10% MeOH/$CH_2Cl_2$); ESI m/z $C_{73}H_{86}N_8O_{24}Si$ 1458.58, found 1459.7;

Compound 8f. 95% yield from compound 7f following the general procedure; silica gel flash chromatography eluent: 5% MeOH/$CH_2Cl_2$; $[\alpha]_D$+11.3° (c 0.8), MeOH)$R_f$ 0.1 (5% MeOH/$CH_2Cl_2$). ESI m/z $C_{73}H_{88}N_6O_{24}Si$ 1432.59, found 1433.4;

Compound 8g. 95% yield from compound 7g following the general procedure; silica gel flash chromatography eluent: 10% MeOH/CH$_2$Cl$_2$; $[\alpha]_D$+11.6° (c 1.1, MeOH); R$_f$ 0.4 (10% MeOH/CH$_2$Cl$_2$);

Compound 8i. 95% yield from compound 9l following the general procedure; silica gel flash chromatography eluent: 5% MeOH/CH$_2$Cl$_2$; $[\alpha]_D$+17.6° (c 0.4, MeOH) R$_f$ 0.3 (5% MeOH/CH$_2$Cl$_2$). ESI m/z C$_{90}$H$_{112}$N$_7$O$_{26}$Si 1734.74 found 1732.1.

Compound 8l. 82% yield from compound 7l following the general procedure; ESI m/z C$_{87}$H$_{102}$N$_6$O$_{24}$Si 1607.82, found 1608.9; $^1$H NMR was taken and is consistent with the structure.

Compound 8m. 79% yield from compound 7m following the general procedure; ESI m/z C$_{87}$H$_{103}$N$_7$O$_{24}$Si 1658.87, found 1659.9; $^1$H NMR was taken and is consistent with the structure.

Compound 8n. 80% yield from compound 7n following the general procedure; ESI m/z C$_{84}$H$_{108}$N$_6$O$_{24}$Si 1613.87, found 1614.9; $^1$H NMR was taken and is consistent with the structure.

Compound 8o. 86% yield from compound 7o following the general procedure; ESI m/z C$_{85}$H$_{105}$N$_7$O$_{24}$Si 1636.86, found 1637.2; $^1$H NMR was taken and is consistent with the structure.

Compound 8p. 82% yield from compound 7p following the general procedure; ESI m/z C$_{86}$H$_{106}$N$_6$O$_{24}$Si 1635.87, found 1636.0; $^1$H NMR was taken and is consistent with the structure.

Compound 8q. 78% yield from compound 7q following the general procedure; ESI m/z C$_{85}$H$_{104}$N$_6$O$_{24}$Si 1621.85, found 1622.1; $^1$H NMR was taken and is consistent with the structure.

Compound 8r. 78% yield from compound 7r following the general procedure; ESI m/z C$_{84}$H$_{102}$N$_6$O$_{25}$Si 1623.82, found 1623.8; $^1$H NMR was taken and is consistent with the structure.

Compound 8s. 81% yield from compound 7s following the general procedure; ESI m/z C$_{89}$H$_{112}$N$_8$O$_{26}$Si 1737.97, found 1738.9; $^1$H NMR was taken and is consistent with the structure.

Compound 8t. 86% yield from compound 7t following the general procedure; ESI m/z C$_{89}$H$_{112}$N$_8$O$_{26}$Si 1737.97, found 1738.2; $^1$H NMR was taken and is consistent with the structure.

Compound 8u. 85% yield from compound 7u following the general procedure; ESI m/z C$_{83}$H$_{111}$N$_7$O$_{24}$Si 1608.81, found 1608.8; $^1$H NMR was taken and is consistent with the structure.

Compound 8v. 72% yield from compound 7v following the general procedure; ESI m/z C$_{84}$H$_{110}$N$_6$O$_{24}$Si 1615.88, found 1615.8; $^1$H NMR was taken and is consistent with the structure.

Compound 8w. 91% yield from compound 7w following the general procedure; ESI m/z C$_{88}$H$_{112}$N$_6$O$_{25}$Si 1681.94, found 1681.6; $^1$H NMR was taken and is consistent with the structure.

Compound 8x. 90% yield from compound 7x following the general procedure; ESI m/z C$_{87}$H$_{108}$N$_6$O$_{24}$Si 1649.90, found 1671.9 (M+Na); $^1$H NMR was taken and is consistent with the structure.

Compound 8y. 84% yield from compound 7y following the general procedure; ESI m/z C$_{88}$H$_{110}$N$_6$O$_{26}$Si 1695.93, found 1695.9; $^1$H NMR was taken and is consistent with the structure.

Compound 8z. 95% yield from compound 7z following the general procedure; ESI m/z C$_{88}$H$_{110}$N$_6$O$_{24}$Si 1663.93, found 1686.1 (M+Na); $^1$H NMR was taken and is consistent with the structure.

Compound 8aa. 81% yield from compound 7aa following the general procedure; ESI m/z C$_{92}$H$_{110}$N$_6$O$_{24}$Si 1711.97, found 1711.9; $^1$H NMR was taken and is consistent with the structure.

Compound 8ab. 73% yield from compound 7ab following the general procedure; ESI m/z C$_{87}$H$_{112}$N$_6$O$_{24}$Si 1652.75, found 1653.7; $^1$H NMR was taken and is consistent with the structure.

Compound 8ac. 80% yield from compound 7ac following the general procedure; ESI m/z C$_{88}$H$_{108}$N$_6$O$_{24}$Si 1661.91, found 1661.6; $^1$H NMR was taken and is consistent with the structure.

Compound 8ad. 87% yield from compound 7ad following the general procedure; ESI m/z C$_{105}$H$_{144}$N$_6$O$_{24}$Si 1902.38, found 1902.2; $^1$H NMR was taken and is consistent with the structure.

Compound 8ae. 70% yield from compound 7e following the general procedure; ESI m/z C$_{92}$H$_{107}$N$_7$O$_{26}$Si 1754.95, found 1755.7; $^1$H NMR was taken and is consistent with the structure.

Compound 8af. 85% yield from compound 7af following the general procedure; ESI m/z C$_{88}$H$_{104}$F$_6$N$_6$O$_{24}$Si 1771.87, found 1771.5; $^1$H NMR was taken and is consistent with the structure.

Compound 8ag. 88% yield from compound 7ag following the general procedure; ESI m/z C$_{95}$H$_{116}$N$_6$O$_{24}$Si 1754.05, found 1756.4; $^1$H NMR was taken and is consistent with the structure.

Compound 8ah. 94% yield from compound 7ah following the general procedure; ESI m/z C$_{87}$H$_{105}$F$_3$N$_6$O$_{24}$Si 1703.87, found 1703.5; $^1$H NMR was taken and is consistent with the structure.

Compound 8ai. 95% yield from compound 7ai following the general procedure; ESI m/z C$_{94}$H$_{130}$N$_6$O$_{24}$Si 1756.15, found 1756.3; $^1$H NMR was taken and is consistent with the structure.

Compound 8aj. 83% yield from compound 7aj following the general procedure; ESI m/z C$_{87}$H$_{108}$N$_6$O$_{25}$Si 1665.9, found 1665.6; $^1$H NMR was taken and is consistent with the structure.

Example 8
General Procedure for Final Deprotection
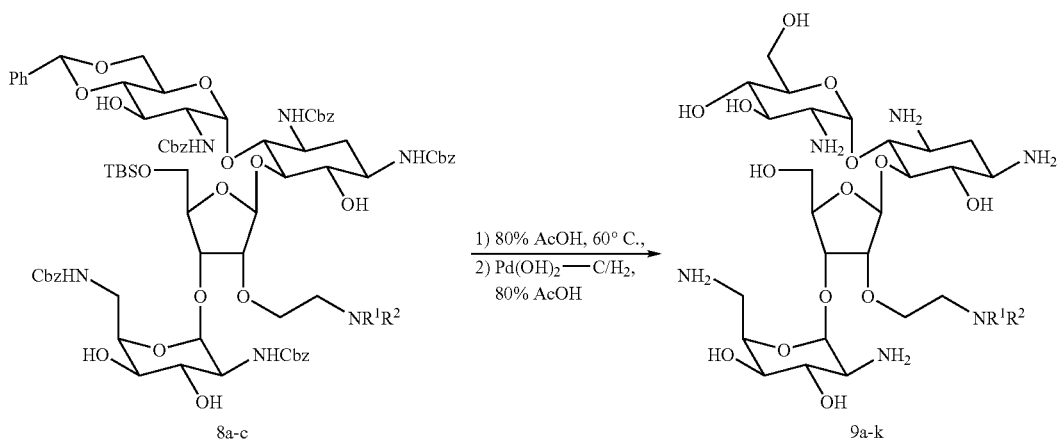
| Compound | R¹ | R² |
|---|---|---|
| 9a (IBIS00560798) | H | 3-pyridyl |
| 9b (IBIS00560799) | H | 3-pyridylmethyl |
| 9c (IBIS00560175) | H | –(CH₂)₃NH₂ (branched) |
| 9d (IBIS00560177) | H | –CH₂CH₂NH₂ |
| 9e (IBIS00560797) | H | benzimidazol-2-ylmethyl |
| 9f (IBIS00560176) | H | H |
| 9g (IBIS00560174) | Me | Me |
| 9h (IBIS00560172) | –(CH₂)₃NH₂ | –(CH₂)₃NH₂ |
| 9i (IBIS00560173) | (R¹ and R² together form homopiperazine) | |

-continued
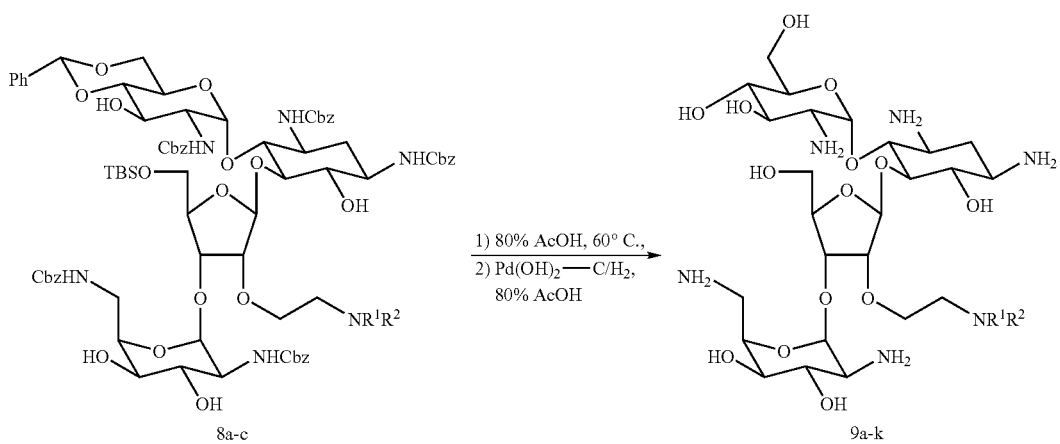
8a-c → 9a-k
1) 80% AcOH, 60° C.,
2) Pd(OH)$_2$—C/H$_2$, 80% AcOH
| Compound | R$^1$ | R$^2$ |
|---|---|---|
| 9j (IBIS00560725) | H | 3-piperidinyl |
| 9k (IBIS00560726) | H | (3-piperidinyl)methyl |
| 9l (IBIS00560932) | H | phenyl |
| 9m (IBIS00560930) | H | 3-quinolinyl |
| 9n (IBIS00560931) | H | cyclohexyl |
| 9o (IBIS00560972) | H | 2-(pyridin-3-yl)ethyl |
| 9p (IBIS00560973) | H | 2-phenylethyl |

-continued
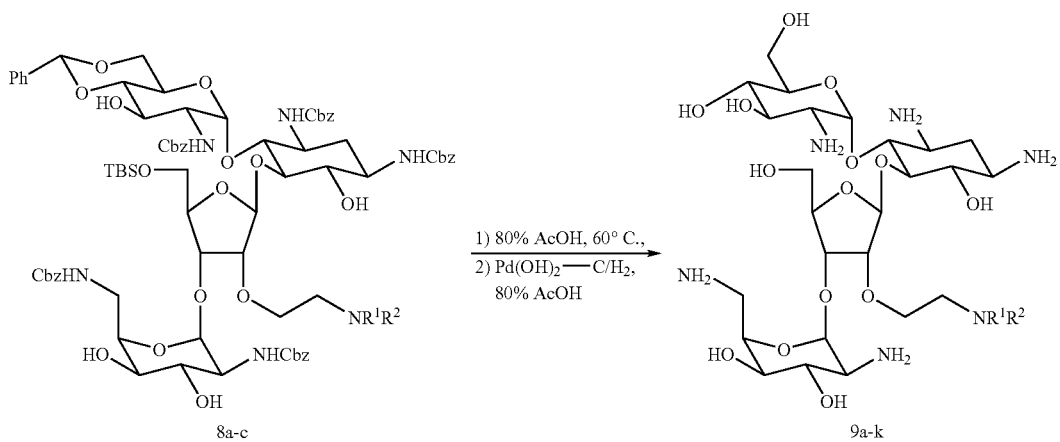
1) 80% AcOH, 60° C.,
2) Pd(OH)$_2$—C/H$_2$, 80% AcOH
| Compound | R$^1$ | R$^2$ |
|---|---|---|
| 9q (IBIS00560974) | H | benzyl (CH$_2$-phenyl) |
| 9r (IBIS00560966) | H | 3-hydroxybenzyl |
| 9s (IBIS00560975) | H | (2-amino-pyridin-5-yl)methyl |
| 9t (IBIS00560965) | H | (2-amino-pyridin-4-yl)methyl |
| 9u (IBIS00561109) | H | 1-(pyridin-2-yl)ethyl |
| 9v (IBIS00561194) | H | 1,3,3-trimethylbutyl |
| 9w (IBIS00561195) | H | 3-hydroxyadamantan-1-yl |
| 9x (IBIS00561144) | H | 3-phenylpropyl |

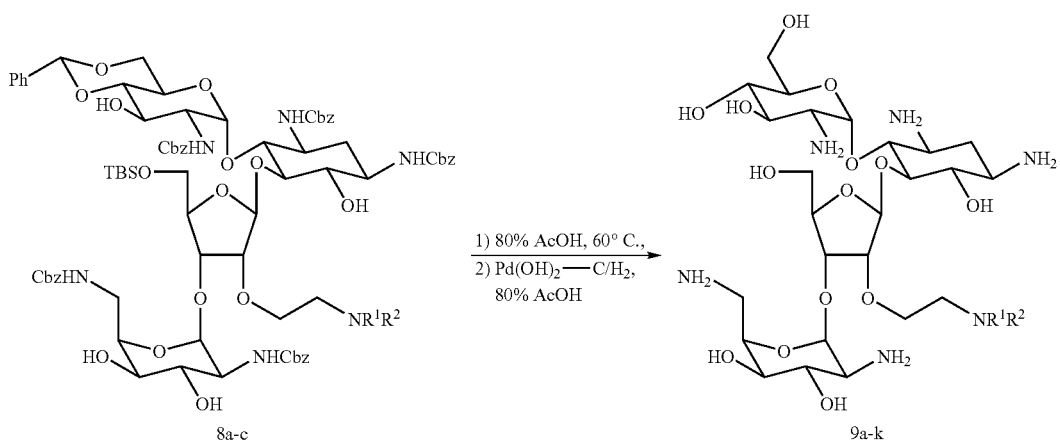
| Compound | R¹ | R² |
|---|---|---|
| 9y (IBIS00561192) | H | 3,5-dimethoxyphenethyl-like group |
| 9z (IBIS00561145) | H | 4-phenylbutyl |
| 9aa (IBIS00561193) | H | 2-(4-biphenyl)ethyl |
| 9ab (IBIS00561951) | H | 2-(norbornyl)ethyl |
| 9ac (IBIS00561950) | H | 1-(1,2,3,4-tetrahydronaphthyl) |
| 9ad (IBIS00561952) | H | cholestanyl |

-continued
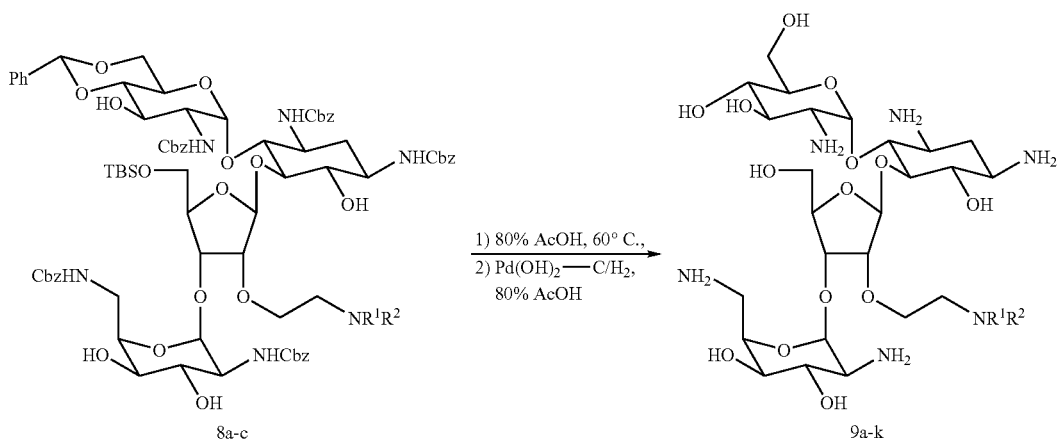
| Compound | R¹ | R² |
|---|---|---|
| 9ae (IBIS00561953) | H | (ethyl-naphthalimide group) |
| 9af (IBIS00561954) | H | (ethyl-3,5-bis(trifluoromethyl)phenyl group) |
| 9ag (IBIS00561969) | (ethyl-phenyl group) | (propyl-phenyl group) |
| 9ah (IBIS00561955) | H | (ethyl-4-trifluoromethylphenyl group) |
| 9ai (IBIS00561972) | (n-nonyl group) | (n-nonyl group) |
| 9aj (IBIS00561971) | H | (ethyl-4-methoxyphenyl group) |

The appropriate substrate was dissolved in 80% aqueous acetic acid (3 mL) and heated at 60° C. for 3 hours The solution was cooled down to room temperature and a catalytic amount of 20% palladium hydroxide on carbon was added and the suspension was stirred at room temperature under an atmosphere of hydrogen (hydrogen balloon) until the conversion of the starting material into the product was completed as indicated by MS analysis. The mixture was filtered through a layer of Celite on cotton, concentrated under vacuum, washed with $CH_2Cl_2$ and lyophilized to afford floppy white solids.

Compound 9a (IBIS00560798). Quantitative yield from compound 8a following the general procedure; $[\alpha]_D$+6.8° (c 0.4, $H_2O$); $^1H$ NMR (400 MHz, $D_2O$) δ 8.00-7.70 (m, 2H), 7.60-7.40 (m, 2H), 5.70 (m, 1H), 5.33 (m, 1H), 5.11 (m, 1H), 4.50 (m, 1H), 4.20-4.00 (m, 4H), 3.85-3.50 (m, 13H), 3.40-3.15 (m, 8H), 2.37 (m, 1H), 1.79 (s, 18H), 1.70 (m, 1H); $^{13}C$ NMR (125 MHz, $D_2O$) δ 181.4, 132.3, 131.6, 129.5, 129.2, 128.7, 127.1, 126.8, 108.8, 96.2, 95.3, 85.3, 81.6, 81.0, 78.0, 74.1, 73.1, 70.7, 69.6, 69.3, 68.0, 67.7, 60.7, 60.3, 54.2, 51.5, 50.3, 49.2, 43.0, 40.7, 29.2, 23.5; ESI m/z $C_{30}H_{53}N_7O_{14}$ 735.37, found 736.5;

Compound 9b (IBIS00560799). Quantitative yield from compound 8b following the general procedure; $[\alpha]_D$+5.4° (c 0.6, $H_2O$); $^1H$ NMR (400 MHz, $D_2O$) δ 7.70-7.30 (m, 4H), 5.71 (m, 1H), 5.38 (m, 1H), 5.16 (m, 1H), 4.55 (m, 1H), 4.20-4.00 (m, 4H), 3.95-3.50 (m, 15H), 3.45-3.15 (m, 8H), 2.32 (m, 1H), 1.81 (s, 18H), 1.65-1.40 (m, 1H); $^{13}C$ NMR (125 MHz, $D_2O$) δ 181.4, 150.5, 140.0, 133.9, 132.8, 129.8, 129.1, 128.9, 128.2, 125.5, 109.0, 96.6, 95.7, 85.7, 81.4, 78.5, 74.3, 73.7, 71.1, 69.9, 68.5, 68.1, 61.0, 60.1, 54.6, 51.6, 50.8, 49.6, 46.6, 41.1, 31.8, 29.7, 23.5; ESI m/z $C_{31}H_{55}N_7O_{14}$ 749.38, found 750.4;

Compound 9c (IBIS00560175). Quantitative yield from compound 8c following the general procedure; $[\alpha]_D$+5.7° (c 0.4, $H_2O$); $^1H$ NMR (400 MHz, $D_2O$) δ 5.72 (m, 1H), 5.44 (m, 1H), 5.21 (m, 1H), 4.59 (m, 1H), 4.20-4.00 (m, 4H), 3.95-3.50 (m, 13H), 3.45-2.7 (m, 14H), 2.26 (m, 1H), 1.87 (s, 21H), 1.59 (m, 1H); $^{13}C$ NMR (125 MHz, $D_2O$) δ 182.2, 108.9, 96.8, 96.0, 86.0, 81.8, 79.8, 74.5, 74.3, 71.3, 71.2, 70.1, 68.6, 68.2, 67.5, 61.0, 54.8, 51.8, 51.1, 50.3, 49.8, 48.8, 45.5, 43.7, 41.1, 37.3, 31.1, 27.4, 24.5, 24; ESI m/z $C_{28}H_{57}N_7O_{14}$ 715.40, found 716.4;

Compound 9d (IBIS00560177). Quantitative yield from compound 8d following the general procedure; [ ]D+8.1° (c 0.6, $H_2O$); $^1H$ NMR (400 MHz, $D_2O$) δ 5.75 (m, 1H), 5.44 (m, 1H), 5.20 (m, 1H), 4.30-4.00 (m, 4H), 3.85-3.50 (m, 13H), 3.40-3.15 (m, 8H), 3.00-2.55 (m, 4H) 2.31 (m, 1H), 1.91 (s, 21H), 1.63 (m, 1H); ESI m/z $C_{27}H_{55}N_7O_{14}$ 701.38, found 702.6;

Compound 9e (IBIS00560797). Quantitative yield from compound 8e following the general procedure; $[\alpha]_D$+8.6° (c 0.7, $H_2O$); $^1H$ NMR (400 MHz, $D_2O$) δ 7.80-7.40 (m, 4H), 5.81 (m, 1H), 5.44 (m, 1H), 5.24 (m, 1H), 4.35-4.10 (m, 4H), 3.95-3.50 (m, 14H), 3.45-3.15 (m, 8H), 2.42 (m, 1H), 1.91 (s, 18H), 1.61 (m, 1H); ESI m/z $C_{33}H_{56}N_8O_{14}$ 788.39, found 789.5;

Compound 9f (IBIS00560176). Quantitative yield from compound 8f following the general procedure; $[\alpha]_D$+10.6° (c 0.7, $H_2O$); $^1H$ NMR (400 MHz, $D_2O$) δ 5.78 (m, 1H), 5.46 (m, 1H), 5.26 (m, 1H), 4.30-4.00 (m, 6H, 3.95-3.50 (m, 14H), 3.45-3.00 (m, 6H), 2.35 (m, 1H), 1.91 (s, 21H), 1.71 (m, 1H); ESI m/z $C_{25}H_{50}N_6O_{14}$ 658.33, found 659.4;

Compound 9g (IBIS00560174). Quantitative yield from compound 8g following the general procedure; $[\alpha]_D$+7.3° (c 0.6, $H_2O$); $^1H$ NMR (400 MHz, $D_2O$) δ 5.76 (m, 1H), 5.46 (m, 1H), 5.26 (m, 1H), 4.62 (m, 1H), 4.41-4.04 (m, 5H, 3.90-3.50 (m, 14H), 3.45-3.20 (m, 6H), 2.9 (s, 6H) 2.33 (m, 1H), 1.88 (s, 18H), 1.70 (m, 1H); $^{13}C$ NMR (125 MHz, $D_2O$) δ 182.0, 108.8, 96.7, 95.6, 85.8, 81.4, 81.2, 78.9, 74.3, 74.2, 73.9, 71.2, 69.9, 69.8, 68.5, 68.0, 64.9, 60.9, 59.9, 57.5, 54.7, 51.7, 50.9, 49.6, 43.6 (2C), 41.1, 30.2, 23.9; ESI m/z $C_{27}H_{54}N_6O_{14}$ 686.4, found 687.4;

Compound 9h (IBIS00560172). Quantitative yield from compound 8h following the general procedure; $[\alpha]_D$+21.5° (c 0.6, $H_2O$); $^1H$ NMR (400 MHz, $D_2O$) δ 5.55 (m, 1H), 5.16 (m, 1H), 5.08 (m, 1H), 4.49 (m, 1H), 4.30-4.00 (m, 5H, 3.95-3.40 (m, 14H), 3.45-3.15 (m, 6H), 2.58 (m, 8H) 2.18 (m, 1H), 1.92 (s, 24H), 1.30 (m, 1H); ESI m/z $C_{29}H_{60}N_8O_{14}$ 744.42, found 745.6;

Compound 9i (IBIS00560173). Quantitative yield from compound 8l following the general procedure; $[\alpha]_D$+14.5° (c 0.7, $H_2O$); $^1H$ NMR (400 MHz, $D_2O$) δ 5.70 (m, 1H), 5.35 (m, 1H), 5.12 (m, 1H), 4.49 (m, 1H), 4.30-4.00 (m, 5H, 3.95-3.40 (m, 14H), 3.45-3.05 (m, 10H), 2.68 (m, 4H), 2.26 (m, 1H), 1.87 (s, 21H), 1.62 (m, 1H); $^{13}C$ NMR (125 MHz, $D_2O$) δ 181.6, 108.9, 96.6, 95.9, 87.5, 81.9, 81.6, 78.5, 74.6, 74.5, 73.7, 71.2, 70.0, 69.8, 68.5, 68.1, 68.0, 61.0, 60.6, 57.2, 54.7, 51.8, 51.1, 50.8, 50.2 (2), 49.7, 43.6 (2C), 41.1, 31.1, 23.6; ESI m/z $C_{29}H_{58}N_7O_{14}$ 728.40, found 728.3;

Compound 9j (IBIS00560725). Prepared by extended hydrogenation via 9a. quant.; $[\alpha]_D$+70.8° (c 1.0, $H_2O$); $^1H$ NMR (400 MHz, $D_2O$) δ 5.66 (m, 1H), 5.30 (m, 1H), 5.11 (m, 1H), 4.46 (m, 1H), 4.20-4.00 (m, 5H, 3.95-3.50 (m, 14H), 3.40-2.95 (m, 11H), 2.37 (m, 1H), 2.1-1.9 (m, 4H) 1.79 (s, 18H), 1.70 (m, 1H); $^{13}C$ NMR (125 MHz, $D_2O$) δ 181.0, 108.9, 96.6, 95.7, 90.9, 85.5, 81.5, 77.7, 74.5, 74.3, 73.3, 71.1, 69.9, 69.5, 68.4, 68.3, 68.0, 61.0, 54.5, 52.4, 51.5, 50.6, 49.4, 44.7, 44.2, 41.0, 40.1, 34.5, 28.9, 23.3 20.9, 20.2; ESI m/z $C_{30}H_{59}N_7O_{14}$ 741.41, found 742.7;

Compound 9k (IBIS00560726). Prepared by extended hydrogenation via 9b. quant.; $[\alpha]_D$+120.4° (c 1.1, $H_2O$); $^1H$ NMR (400 MHz, $D_2O$) δ, 5.67 (m, 1H), 5.32 (m, 1H), 5.25 (m, 1H), 4.48 (m, 1H), 4.20-4.00 (m, 5H), 3.95-3.30 (m, 18H), 3.30-3.00 (m, 12H), 2.21 (m, 1H), 1.81 (s, 21H), 1.62 (m, 1H); $^{13}C$ NMR (125 MHz, $D_2O$) δ 180.3, 108.5, 96.2, 95.2, 85.0, 81.1, 80.8, 77.2, 74.1 (2C), 72.9, 70.7, 69.4, 69.1, 67.9, 67.5, 60.5, 60.1, 54.1, 51.1, 50.3, 50.2, 49.1, 48.9, 46.1, 44.2, 44.1, 40.6, 30.3, 28.6, 22.75, 22.1, 21.4, 18.2; ESI m/z $C_{31}H_{61}N_7O_{14}$ 755.42, found 756.7.

Compound 9l. 80% yield from compound 8l following the general procedure; ESI m/z $C_{31}H_{54}N_6O_{14}$ 734.79, found 735.5; $^1H$ NMR is consistent with the structure.

Compound 9m. 85% yield from compound 8m following the general procedure; ESI m/z $C_{34}H_{55}N_7O_{14}$ 785.84, found 786.5; $^1H$ NMR is consistent with the structure.

Compound 9n. 85% yield from compound 8n following the general procedure; ESI m/z $C_{31}H_{60}N_6O_{14}$ 740.84, found 741.5; $^1H$ NMR is consistent with the structure.

Compound 9o. 85% yield from compound 8o following the general procedure; ESI m/z $C_{32}H_{57}N_7O_{14}$ 763.83, found 764.7; $^1H$ NMR is consistent with the structure.

Compound 9p. 80% yield from compound 8p following the general procedure; ESI m/z $C_{33}H_{58}N_6O_{14}$ 762.85, found 763.6; $^1H$ NMR is consistent with the structure.

Compound 9q. 85% yield from compound 8q following the general procedure; ESI m/z $C_{32}H_{56}N_6O_{14}$ 748.82, found 749.6; $^1H$ NMR is consistent with the structure.

Compound 9r. 85% yield from compound 8r following the general procedure; ESI m/z $C_{31}H_{54}N_6O_{15}$ 750.79, found 751.6; $^1H$ NMR is consistent with the structure.

Compound 9s. 60% yield from compound 8s following the general procedure; ESI m/z $C_{31}H_{56}N_8O_{14}$ 764.82, found 765.6; $^1H$ NMR is consistent with the structure.

Compound 9t. 65% yield from compound 8t following the general procedure; ESI m/z $C_{31}H_{56}N_8O_{14}$ 764.82, found 765.6; $^1$H NMR is consistent with the structure.

Compound 9u. 75% yield from compound 8u following the general procedure; ESI m/z $C_{30}H_{53}N_7O_{14}$ 735.78, found 736.5; $^1$H NMR is consistent with the structure.

Compound 9v. 80% yield from compound 8v following the general procedure; ESI m/z $C_{31}H_{62}N_6O_{14}$ 742.86, found 743.4; $^1$H NMR is consistent with the structure.

Compound 9w. 80% yield from compound 8w following the general procedure; ESI m/z $C_{35}H_{64}N_6O_{15}$ 808.91, found 809.4; $^1$H NMR is consistent with the structure.

Compound 9x. 90% yield from compound 8x following the general procedure; ESI m/z $C_{34}H_{60}N_6O_{14}$ 776.87, found 777.6; $^1$H NMR is consistent with the structure.

Compound 9y. 90% yield from compound 8y following the general procedure; ESI m/z $C_{35}H_{62}N_6O_{16}$ 822.90, found 823.5; $^1$H NMR is consistent with the structure.

Compound 9z. 90% yield from compound 8z following the general procedure; ESI m/z $C_{35}H_{62}N_6O_{14}$ 790.90, found 791.7; $^1$H NMR is consistent with the structure.

Compound 9aa. 85% yield from compound 8aa following the general procedure; ESI m/z $C_{39}H_{62}N_6O_{14}$ 838.94, found 839.5; $^1$H NMR is consistent with the structure.

Compound 9ab. 80% yield from compound 8ab following the general procedure; ESI m/z $C_{34}H_{64}N_6O_{14}$ 780.90, found 781.5; $^1$H NMR is consistent with the structure.

Compound 9ac. 90% yield from compound 8ac following the general procedure; ESI m/z $C_{35}H_{60}N_6O_{14}$ 788.88, found 789.5; $^1$H NMR is consistent with the structure.

Compound 9ad. 80% yield from compound 8ad following the general procedure; ESI m/z $C_{52}H_{96}N_6O_{14}$ 1029.35, found 1029.7; $^1$H NMR is consistent with the structure.

Compound 9ae. 75% yield from compound 8ae following the general procedure; ESI m/z $C_{39}H_{59}N_7O_{16}$ 881.92, found 882.5; $^1$H NMR is consistent with the structure.

Compound 9af. 90% yield from compound 8af following the general procedure; ESI m/z $C_{35}H_{56}F_6N_6O_{14}$ 898.84, found 899.4; $^1$H NMR is consistent with the structure.

Compound 9ag. 90% yield from compound 8ag following the general procedure; ESI m/z $C_{48}H_{68}N_6O_{14}$ 881.02, found 883.8; $^1$H NMR is consistent with the structure.

Compound 9ah. 85% yield from compound 8ah following the general procedure; ESI m/z $C_{34}H_{57}F_3N_6O_{14}$ 830.84, found 831.5; $^1$H NMR is consistent with the structure.

Compound 9ai. 80% yield from compound 8ai following the general procedure; ESI m/z $C_{41}H_{82}N_6O_{14}$ 883.12, found 883.9; $^1$H NMR is consistent with the structure.

Compound 9aj. 90% yield from compound 8aj following the general procedure; ESI m/z $C_{34}H_{60}N_6O_{15}$ 792.87, found 793.7; $^1$H NMR is consistent with the structure.

Example 9

Preparation of Compounds 10 and 11

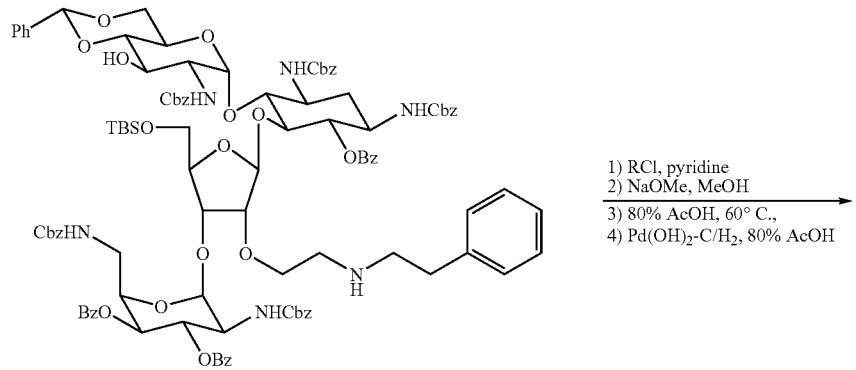

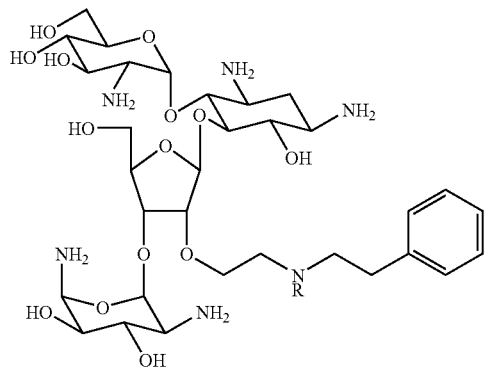

10: R = Bz
11: R = Ac

Compound 7p is treated with the appropriate acyl chloride (1.2 equiv) and then deprotected according to the general procedure to give 10 (benzoyl chloride) and 11 (acetyl chloride).

Compound 10 (IBIS00561197). 75% yield from compound 7p and benzoyl chloride following the general procedure; ESI m/z $C_{40}H_{62}N_6O_{15}$ 866.97, found 867.5; $^1$H NMR is consistent with the structure.

Compound 11 (IBIS00561196). 80% yield from compound 7p and acetyl chloride following the general procedure; ESI m/z $C_{35}H_{60}N_6O_{15}$ 804.88, found 806.3; $^1$H NMR is consistent with the structure.

Example 10

Preparation of Compound 12

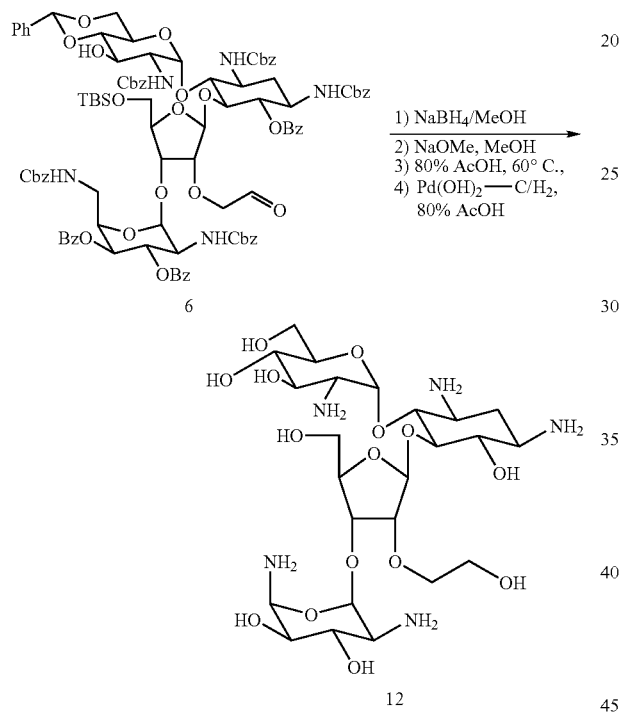

Compound 6 is treated with 5-10 equivalents of sodium borohydride in methanol, and then deprotected according to the general procedure to give compound 12.

Compound 12 (IBIS00560724). 80% yield; ESI m/z $C_{25}H_{49}N_5O_{15}$ 659.68, found 660.51; $^1$H NMR is consistent with the structure.

Example 11

Preparation of Compound 13

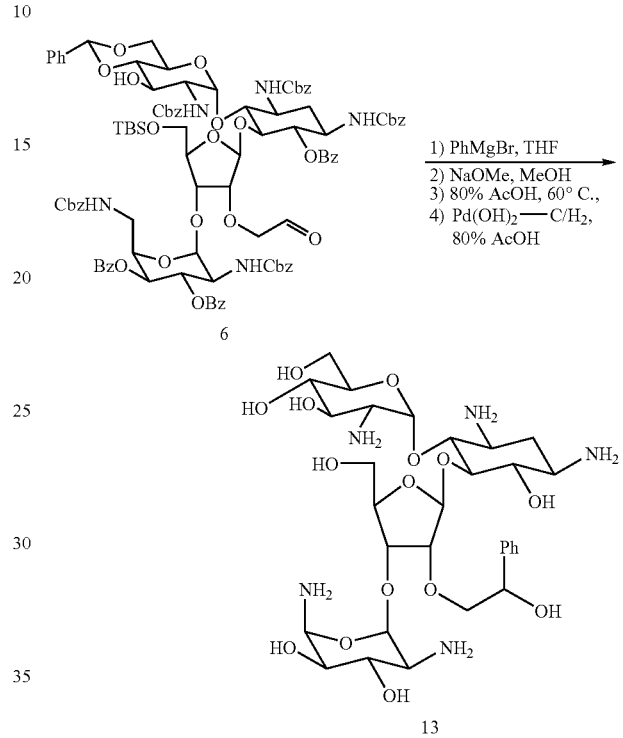

Compound 6 is treated with 1-2 equivalents of Phenylmagnesiumbromide in THF, and then deprotected according to the general procedure to give compound 13.

Compound 13 (IBIS00560281). 65% yield; ESI m/z $C_{31}H_{53}N_5O_{15}$ 735.78, found 736.8; $^1$H NMR is consistent with the structure.

Example 12

Preparation of Compound 15

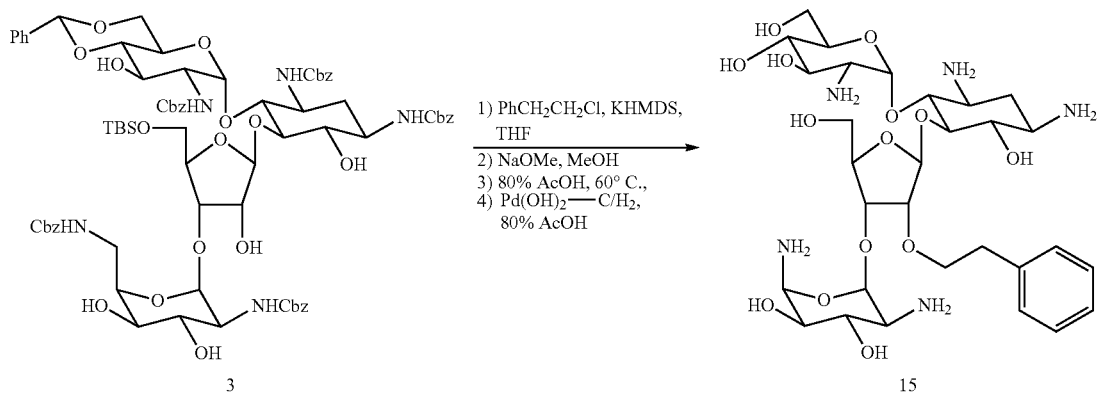

Compound 3 (2.10 g, 1.411 mmol) was dissolved in dry THF (70 mL) and phenethyl chloride (10 equiv) was added followed by the dropwise addition of 0.5 M KHMDS solution in toluene (1.411 mL, 0.706 mmol). The mixture was stirred for overnight at room temperature, and then deprotected according to the general procedures to provide phenethyl ether 15.

Compound 15 (IBIS00560282). 85% yield; ESI m/z $C_{31}H_{53}N_5O_{14}$ 719.78, found 720.9; $^1$H NMR is consistent with the structure.

Example 13

Coupled Bacterial Transcription/Translation Assay

The DNA template, pBestLuc™ (Promega), is a plasmid containing a reporter gene for firefly luciferase fused to a strong tac promoter and ribosome binding site. Messenger RNA from 1 µg pBestLuc is transcribed and translated in *E. coli* S30 bacterial extract in the presence or absence of test compound. Compounds are tested in a black 96 well microtiter plate with an assay volume of 35 µL. Each test well contains: 5 µL test compound, 13 µL S30 premix (Promega), 4 µL 10× complete amino acid mix (1 mM each), 5 µL *E. coli* S30 extract and 8 µL of 0.125 µg/µL pBestLuc™. The transcription/translation reaction is incubated for 35 minutes at 37° C. followed by detection of functional luciferase with the addition of 30 µL LucLite™ (Packard). Light output is quantitated on a Packard TopCount.

Example 14

Mass Spectrometry Based Binding Assay

Screening was performed by measuring the formation of non-covalent complexes between a single ligand or ligand mixture and the appropriate RNA target, such as for example the 16S Kd and 18S Kd ribosomal subunits, along with suitable control structured RNA target(s) simultaneously using a 9.4 T FT-ICR mass spectrometer as detector. Full experimental details of the assay for have been described in related literature (Sannes-Lowery, et al. in *TrAC, Trends Anal Chem.* 2000, 19, 481-491; Sannes-Lowery, et al. in *Anal. Biochem.* 2000, 280, 264-271; and Griffey, R. H.; Sannes-Lowery, K. A.; Drader, J. J.; Mohan, V.; Swayze, E. E. et al. Characterization of Low Affinity Complexes Between RNA and Small Molecules Using Electrospray Ionization Mass Spectrometry. J. Am. Chem. Soc. 2000, 122, 9933-9938).

In a typical experiment, 10 µL of an aqueous solution containing 100 mM ammonium acetate buffer, 2.5 or 5 µM of each RNA, and 33% isopropyl alcohol (to aid ion desolvation) was prepared with different concentrations of each ligand or ligand mixture. Samples were introduced into the electrospray ionization source (negative ionization mode) at 1 µL/min and ions were stored for 1 sec in an RF-only hexapole following desolvation. The abundances were integrated from the respective ions for free RNA and the ligand-RNA complex. The primary (1:1 RNA:ligand) and secondary (1:2 complex, if observed). KD values were determined by titrating a single ligand through a concentration range of 0.25-25 µM with an RNA target concentration of 0.10 µM. The peak ratios were measured at each concentration, then a plot of complex/free RNA versus concentration of ligand added was fitted to a second (or higher) order binding polynomial to determine the KD.

Example 15

In Vitro Antibacterial Activity Determination of Minimum Inhibitory Concentrations (MICs)

The MIC assays are carried out in 150 µL volume in duplicate in 96-well clear flat-bottom plates. The bacterial suspension from an overnight culture growth in appropriate medium is added to a solution of test compound in 4% DMSO in water. Final bacterial inoculum is approximately $10^5$-$10^6$ CFU/well. The percent growth of the bacteria in test wells relative to that observed for a well containing no compound is determined by measuring absorbance at 595 nm ($A_{595}$) after 24 h. The MIC is determined as a range of single compound where the complete inhibition of growth is observed at the higher concentration and cells are viable at the lower concentrations. Both ampicillin and tetracycline are used as antibiotic-positive controls in each screening assay for *S. pyogenes, E. coli* imp-, *E. coli, S. aureus, E. faecalis, K. pneumoniae* and *P. vulgaris*. Ciprofloxacin is used as an antibiotic positive control in each screening assay for *P. aeruginosa*.

Example 16

Representative Aminoglycoside Compounds

The following compounds were prepared using methods illustrated in the previous examples. The compounds were also examined in standard bacterial assays against *E. Coli* and *S. Aureus* to determine activities.

| IBIS # | 16 s kD (µm) | Trans/trans IC50 (µm) | MIC (µm) E. Coli | MIC (µm) S. Aureus |
|---|---|---|---|---|
| 00560172 | 9.2 | 1.0 | >50 | 25-50 |
| 00560173 | 1.3 | 0.18 | 25-50 | 2-3 |
| 00560174 | 0.93 | 0.21 | 12-52 | 6-12 |
| 00560175 | 0.37 | 0.29 | 25-50 | 3-6 |
| 00560175 | 0.10 | 0.29 | 25 | 3 |
| 00560176 | 0.27 | 0.35 | 12-25 | 2-3 |
| 00560177 | 0.71 | 0.29 | 6-12 | 2-3 |
| 00560177 | 0.23 | 0.29 | 6 | 2 |
| 00560281 | 2.7 | 0.26 | 25-50 | 3-6 |
| 00560282 | 3.8 | 0.34 | >50 | 6-12 |
| 00560721 | 75 | 0.08 | 25-50 | 25-50 |
| 00560722 | 19 | 0.17 | 6-12 | 12-25 |
| 00560724 | 0.93 | 0.06 | 12-25 | 6-12 |
| 00560725 | 0.11 | 0.08 | 1.5-3 | 3-6 |
| 00560726 | 0.25 | 0.04 | 1.5-3 | 3-6 |
| 00560726 | 0.13 | 0.23 | 5 | 1 |
| 00560797 | 4.1 | 0.34 | 6-12 | 25-50 |
| 00560798 | 0.55 | 0.08 | 3-6 | 0.6-1 |
| 00560799 | 0.87 | 0.08 | 6-12 | 0.6-1 |

Example 17

Representative Aminoglycoside Compounds

The following compounds were prepared using methods illustrated in the previous examples. The compounds were analyzed for their activity using FTICR mass spectrometry and a bacterial transcription/translation assay, such as described herein. The compounds were also examined in standard bacterial assays against *E. Coli* and *S. Aureus* to determine activities.

| IBIS# | 18 S Kd (μM) | 16 S Kd (μM) | Trans/Trans IC50 (μM) | MIC (μM) E. Coli. | MIC (μM) S. Aureus |
|---|---|---|---|---|---|
| 00560930 | 0.9 | 0.1 | 0.1 | 12-25 | 1-2 |
| 00560931 | 0.4 | 0.1 | 0.2 | 3-6 | 3-5 |
| 00560932 | NA | NA | 0.1 | 50-100 | 6-12 |
| 00560965 | 0.3 | 0.02 | 0.7 | 6-12 | 0.6-1 |
| 00560966 | 1.8 | 0.6 | 0.3 | 12-25 | 2-3 |
| 00560972 | 1.0 | 0.2 | 0.2 | 6-12 | 0.6-1 |
| 00560973 | 1.3 | 0.1 | 1.1 | 3-6 | 0.3-0.6 |
| 00560974 | 0.3 | 0.1 | 0.8 | 3-6 | 3-5 |
| 00560975 | 0.5 | 0.1 | 0.2 | 3-6 | 0.3-0.6 |
| 00561109 | 22 | 5 | 0.4 | 12-25 | 1-2 |
| 00561144 | 6.3 | 1.0 | 0.1 | 3-5 | 0.6-1.2 |
| 00561145 | 6.4 | 0.7 | 0.1 | 3-5 | 0.6-1.2 |
| 00561146 | 59.0 | 40 | 0.2 | 10-20 | 3-5 |

Example 18

Representative Aminoglycoside Compounds

The following compounds were prepared using methods illustrated in the pervious examples. The compounds were analyzed for their activity using FTICR mass spectrometry and a bacterial transcription/translation assay, such as described herein. The compounds were also examined in standard bacterial assays against *E. Coli* and *S. Aureus* to determine activities.

| IBIS# | 18 S Kd (μM) | 16 S Kd (μM) | Trans/Trans IC50 (μM) | MIC (μM) E. Coli. | MIC (μM) S. Aureus |
|---|---|---|---|---|---|
| 00561192 | NA | NA | 0.2 | 10-20 | 5-10 |
| 00561193 | 3.5 | 0.9 | 1.5 | 20-40 | 5-10 |
| 00561194 | 5.8 | 2.5 | 0.3 | 10-20 | 0.6-1 |
| 00561195 | 1.7 | 3.2 | 0.4 | 20-40 | 1-3 |
| 00561196 | 6.1 | 1.5 | 0.4 | 10-20 | 1-3 |
| 00561197 | 2.5 | 3.9 | 0.4 | 10-20 | 3-5 |

Example 19

Representative Aminoglycoside Compounds

The following compounds were prepared using methods illustrated in the previous examples. The compounds were also examined in standard bacterial assays against *E. Coli* and *S. Aureus* to determine activities. If present, "N.D." indicates "no data".

| IBIS# | MIC (μM) E. Coli. | MIC (μM) S. Aureus |
|---|---|---|
| 00561950 | >10 | 1.25-2.5 |
| 00561951 | >10 | 5.0-10.0 |
| 00561952 | >10 | 2.5-5.0 |
| 00561953 | N.D. | N.D. |
| 00561954 | >10 | 2.5-5.0 |
| 00561955 | 5.0-10.0 | 0.6-1.2 |

Example 20

Representative Aminoglycoside Compounds

The following compounds were prepared using methods illustrated in the previous examples. The compounds were also examined in standard bacterial assays against *E. Coli, S. Aureus, P. aurginosa, K. pneumoniae, P. vulgaris*, and *A. baumannii* to determine activities. Each of the bacterial cultures that are available from ATCC (www.atcc.org) is identified by its ATCC number. *A. baumannii* is gentamicin sensitive *Acinetobacter baumannii* #2 from Walter Reed.

| | MIC (μM) | | | |
|---|---|---|---|---|
| IBIS# | E. coli ATCC (25922) | S. aureus ATCC(13709) | P. aurginosa ATCC(25416) | P. aurginosa ATCC(29248) |
| 00561969 | 10-20 | 0.6-1.2 | 10-20 | >40 |
| 00561971 | 5-10 | <0.6 | >40 | >40 |
| 00561972 | 5-10 | 1.2-2.5 | 2.5-5.0 | 20-40 |

| | MIC (μM) | | |
|---|---|---|---|
| | K. pneumoniae ATCC (10031) | P. vulgaris ATCC(8427) | A. baumannii WReed 2 |
| 00561969 | 2.5-5.0 | 10-20 | 10-20 |
| 00561971 | 1.2-2.5 | 5-10 | 2.5-5.0 |
| 00561972 | 2.5-5.0 | 5-10 | 10-20 |

Example 21

Animal and In Vivo Studies

Male ICR mice are fed with autoclaved commercial food pellets and sterile water ad libitum. Animals are inoculated intraperitoneally with $1.0 \times 10^6$ CFU/0.5 mL/mouse of *S. aureus* (ATCC 13709) containing 10% mucin. Ten animals each are randomly assigned to either control or treatment groups. Test compound and gentamycin (included as a positive control) are both administered subcutaneously one and 3 hour after infection. Test compound is administered as an aqueous buffer solution (phosphate buffered saline (PBS), pH=7.4). The data is presented as the number of mice out of the 10 in the group that were not protected from lethal infection. The data in the table below clearly indicates that both 560973 and 560799 are effective at preventing lethal bacterial infections in mice, with 560973 being protective at doses as small as 0.25 mg/kg.

| Compound | (mg/kg) | | | | | | | | | |
| --- | --- | --- | --- | --- | --- | --- | --- | --- | --- | --- |
| | 0.1 | 0.25 | 0.5 | 1 | 2 | 4.5 | 9 | 18 | 37 | 75 |
| 560973 | 5/10 | 1/10 | 0/10 | 0/10 | 0/10 | 0/10 | 0/10 | 0/10 | 0/10 | 0/10 |
| 560799 | 7/10 | 6/10 | 3/10 | 0/10 | 0/10 | 0/10 | 0/10 | 0/10 | 0/10 | 0/10. |

What is claimed is:

1. A compound of formula I:

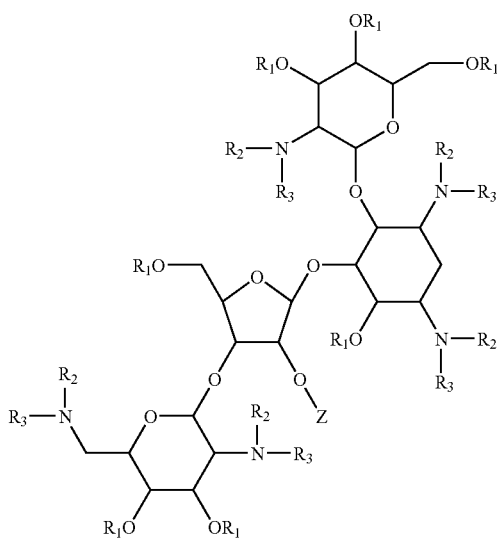

wherein:
each $R_1$ is, independently, H or a hydroxyl protecting group;
each $R_2$ and $R_3$ is, independently, H, an amino protecting group or together $R_2$ and $R_3$ that are connected to the same nitrogen atom form a cyclic protecting group that can include additional heteroatoms selected from N, O and S;
Z has the formula:

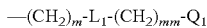

wherein:
$L_1$ is S, O or $NJ_1$;
m is from 1 to about 8;
mm is 0 or from 1 to about 8;
$Q_1$ is H, OH, halogen, $NJ_1J_2$, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl, substituted $C_5$-$C_{20}$ aryl, heteroaryl, substituted heteroaryl, a heterocyclic radical, a substituted heterocyclic radical or a substituted or unsubstituted mono or poly cyclic structure that can be unsaturated, partially saturated or fully saturated and can include one or more heteroatoms selected from O, N and S;
each of said substituted groups, is, independently, mono or poly substituted with substituent groups selected from halogen, hydroxyl, $C_1$-$C_{20}$ alkyl, substituted $C_1$-$C_{20}$ alkyl, $C_{2-20}$ alkenyl, substituted $C_2$-$C_{20}$ alkenyl, $C_2$-$C_{20}$ alkynyl, substituted $C_2$-$C_{20}$ alkynyl, $C_5$-$C_{20}$ aryl or substituted $C_5$-$C_{20}$ aryl, heteroaryl or a substituted heteroaryl, haloalkyl, alkoxy, thioalkoxy, haloalkoxy, —$NJ_1J_2$, azido, carboxy, acyl, =O, cyano, nitro, mercapto, sulfide, sulfonyl and sulfoxide and wherein said substituent groups are optionally protected; and
$J_1$ and $J_2$ are each, independently, H, $C_1$-$C_{20}$ alkyl, substituted $C_1$-$C_{20}$ alkyl, $C_1$-$C_{20}$ aminoalkyl or an amino protecting group or $J_1$ and $J_2$ are joined in a heterocyclic compound including the nitrogen atom connecting them and optionally including from 1 to 2 additional heteroatoms selected from O, N, and S.

2. The compound of claim 1 wherein each $R_1$ is a hydroxyl protecting group.

3. The compound of claim 1 wherein each $R_1$ is H.

4. The compound of claim 1 wherein each $R_2$ is an amino protecting group and each $R_3$ is H, or optionally $R_2$ and $R_3$ that are connected to the same nitrogen atom form a cyclic protecting group that may include additional heteroatoms selected from N, O and S.

5. The compound of claim 1 wherein each $R_1$, $R_2$ and $R_3$ is H.

6. The compound of claim 1 wherein m is from 2 to 8.

7. The compound of claim 1 wherein the sum of m and mm is from 3 to 8.

8. The compound of claim 1 wherein m is 2 and $L_1$ is $NJ_1$.

9. The compound of claim 8 wherein mm is from 1 to 4.

10. The compound of claim 9 wherein $Q_1$ is $NJ_1J_2$ or a substituted or unsubstituted mono or poly cyclic structure that can be unsaturated, partially saturated or fully saturated and can include one or more heteroatoms selected from O, N and S.

11. The compound of claim 10 wherein said substituted or unsubstituted mono or poly cyclic structure comprises one or more fused or linked rings wherein each ring is, independently, alicyclic, heterocyclic, aryl or heteroaryl.

12. The compound of claim 1 wherein $Q_1$ is phenyl, biphenyl, benzoyl, adamanthanyl, a steroidyl group, 1,8-naphthalenedicarboximide, pyridinyl, piperidinyl, piperazinyl, benzimidazolyl, imidazolyl, pyrrolidinyl, pyrazolyl, indolyl, 1H-indazolyl, α-carbolinyl, carbazolyl, phenothiazinyl, phenoxazinyl, quinolinyl, tetrazolyl, triazolyl, and morpholinyl.

13. The compound of claim 1 wherein m is from 1 to 5.

14. The compound of claim 1 wherein mm is 0.

15. The compound of claim 14 wherein $Q_1$ is a substituted or unsubstituted mono or poly cyclic structure that can be unsaturated, partially saturated or fully saturated and can include one or more heteroatoms selected from O, N and S.

16. The compound of claim 15 wherein said substituted or unsubstituted mono or poly cyclic structure comprises one or more fused or linked rings wherein each ring is, independently, alicyclic, heterocyclic, aryl or heteroaryl.

17. The compound of claim 16 wherein said mono or poly cyclic structure is a heterocycle radical, aryl or a heteroaryl group.

18. The compound of claim 1 wherein m is 2.

19. The compound of claim 8 wherein $J_1$ is H.

20. The compound of claim 1 wherein m is 2, $L_1$ is $NJ_1$ and mm is from 1 to 4.

21. The compound of claim 1 having the configuration:
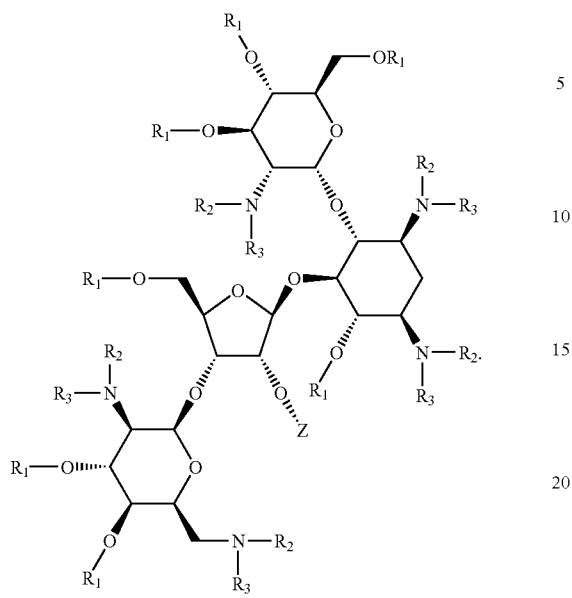
22. The compound of claim 1 for use in therapy.
23. A method of treating a bacterial infection in a mammal comprising administering to the mammal an effective amount of a compound of claim 1.
* * * * *